(12) United States Patent
Kubota et al.

(10) Patent No.: US 7,812,044 B2
(45) Date of Patent: *Oct. 12, 2010

(54) ANTICANCER AGENTS

(75) Inventors: Yoshinobu Kubota, Yokohama (JP); Hiroji Uemura, Yokohama (JP); Noboru Nakaigawa, Yokohama (JP); Kenichiro Naito, Mino (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1359 days.

This patent is subject to a terminal disclaimer.

(21) Appl. No.: 10/495,217

(22) PCT Filed: Nov. 12, 2002

(86) PCT No.: PCT/JP02/11780
§ 371 (c)(1),
(2), (4) Date: May 12, 2004

(87) PCT Pub. No.: WO03/041739
PCT Pub. Date: May 22, 2003

(65) Prior Publication Data
US 2005/0119323 A1    Jun. 2, 2005

(30) Foreign Application Priority Data
Nov. 13, 2001   (JP)   ............................ 2001-348004
Apr. 16, 2002   (JP)   ............................ 2002-113959

(51) Int. Cl.
*A61K 31/41*   (2006.01)
(52) U.S. Cl. ..................................... 514/381
(58) Field of Classification Search ............... 514/381
See application file for complete search history.

(56) References Cited

U.S. PATENT DOCUMENTS 6,004,989 A * 12/1999 Naka et al. ............... 514/381
6,641,811 B1 * 11/2003 Suthanthiran et al. ..... 424/146.1
6,833,381 B2 * 12/2004 Ikeya et al. ................ 514/397

FOREIGN PATENT DOCUMENTS

| EP | 1 136 079 | 9/2001 |
| EP | 1 258 254 | 11/2002 |
| JP | 2000-159621 | 6/2000 |
| WO | 99/44590 | 9/1999 |
| WO | 00/38676 | 7/2000 |

OTHER PUBLICATIONS

Gura et al. Systems for identifying new drugs are often faulty. Science, 1997, 278:1041-1042.*
Johnson et al. Relationships between drug activity in NCI preclinical in vitro and in vivo models and early clinical trials. British J. of Cancer, 2001, 84(10):1424-1431.*
Chamberlain et al. Innovations and strategies for the development of anticancer vaccines. Expert Opinion on Pharmacology, 2000, vol. 1, pp. 603-614.*
Kosaka et al. Prostate, 2007, vol. 67, No. 1, pp. 41-49 (Abstract attached).*
Pollard, M. Cancer Letters, 1997, vol. 111, pp. 221-224.*
Newling, D.W. Prostate Cancer and Prostatic Diseases, 2000, vol. 3, pp. 290-295.*
Y. Fujimoto et al., "Angiotension II type 1 receptor expression in human pancreatic cancer and growth inhibition by angiotension II type 1 receptor antagonist", FEBS Letters, vol. 495, No. 3, pp. 197-200, 2001.
E. R. Inwang et al., "Antiotension II type 1 receptor expression in human breast tissues", British Journal of Cancer, vol. 75, No. 9, pp. 1279-1283, 1997.
D. A. Goldfarb et al., "Antiotension II receptor subtypes in the human renal cortex and renal cell carcinoma", The Journal of Urology, vol. 151, pp. 208-213, Jan. 1994.
S. Marsigliante et al., "AT1 angiotension II receptor subtype in the human larynx and squamous laryngeal carcinoma", Cancer Letters, vol. 110, pp. 19-27, 1996.

* cited by examiner

*Primary Examiner*—James D Anderson
(74) *Attorney, Agent, or Firm*—Wenderoth, Lind & Ponack, L.L.P.

(57) ABSTRACT

Remedies/preventives for hormone-independent cancer, hormone-independent cancer cell proliferation inhibitors, apoptosis inducers for cancer cells, etc. each containing a compound having an angiotensin II antagonism, its prodrug or a salt thereof. Thus, excellent anticancer agents are provided.

10 Claims, 11 Drawing Sheets

Fig. 10

List of cases

| Case | Age | Metastasized lesion | Initial therapy | PSA Maximum | PSA Minimum | Response reduction value |
|---|---|---|---|---|---|---|
| 1 | 7 7 | Bone, lung | Hormone therapy | 684 | 19.4 | (+) |
| 2 | 7 7 | Bone, lung | ope, Hormone therapy | 374 | 122 | (+) |
| 3 | 7 5 | Bone | Hormone therapy | 1140 | 987 | (+) |
| 4 | 8 1 | Bone, Lymph node | Hormone therapy | 417 | 249 | (+) |
| 5 | 6 5 | Bone | Hormone therapy | 5.2 | 2.5 | (+) |
| 6 | 6 5 | Bone | Hormone therapy | PD | | (-) |
| 7 | 7 0 | (−) | Hormone therapy, RTx | PD | | (-) |
| 8 | 6 3 | Bone, Lymph node | Hormone therapy, RTx | PD | | (-) |
| 9 | 7 5 | Bone, Lymph node | Hormone therapy, RTx | PD | | (-) |
| 1 0 | 6 8 | Bone, Lymph node | Hormone therapy, RTx | PD | | (-) |
| 1 1 | 6 3 | Bone, Lymph node | Hormone therapy | PD | | (-) |

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
gtagccaaag tcacctgcat c                                             21

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
cagtcacgta tgatgcctag t                                             21

<210> SEQ ID NO 3
<211> LENGTH: 44
<212> TYPE: DNA
<213> ORGANISM: Artificial Sequence
<220> FEATURE:
<223> OTHER INFORMATION: primer

<400> SEQUENCE: 3
taatacgact cactataggg agagcgggaa atcgtgcgta catt                    44

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
gatggagttg aaggtagttt cgtg                                          24

ANTICANCER AGENTS

This application is a U.S. national stage of international Application No. PCT/JP02/11780 filed Nov. 12. 2002.

TECHNICAL FIELD

The present invention relates to remedies/preventives for hormone-independent cancer, hormone-independent cancer cell proliferation inhibitors, apoptosis inducers for cancer cells, etc. each containing a compound having an angiotensin II antagonism (AII antagonism) or a salt thereof, or its prodrug.

BACKGROUND ART

Currently, medical castration using hormone drugs is widely used for cancer therapy, but there are cancers which do not respond to hormone drugs (hormone-independent cancer). Also in hormone-dependent cancers exhibiting effects in hormone therapy, it is known that when therapy is continued, hormone-dependent cancers change into hormone-independent cancers by proliferation of hormone-independent cancers (Laboratory Investigation 67, 540, 1992).

Therefore, in therapy for cancers (in particular, prostate cancer, breast cancer, etc.), it is ideal that drugs are properly used according to a type of cancer such as cancer which responds to hormone therapy and cancer which does not respond to hormone therapy, a stage of cancer disease, an age, etc. of an individual patient. However, a method of effectively treating hormone-independent cancers has not been heretofore known.

Apoptosis refers to, for example, cell shrinkage, chromatin condensation, nucleus concentration, disappearance of microvillus on the cell surface, plasma membrane blebbing, apoptotic body formation, gap between peripheral cells accompanied with cell shrinkage, and removal by phagocytes (Japan Clinic, vol. 54, No. 7 (1996)). Apoptosis or programmed cell death plays an important role in individual development and homeostasis maintenance in a living body. It has been gradually made clear that abnormality of apoptosis causes diseases such as cancers, autoimmune diseases and nervous diseases.

Benzimidazole derivatives having an AII antagonism are known as remedies for hypertension, cardiac diseases (hypercardia, heart failure, cardiac infarction etc.), cerebral apoplexy, and circulatory diseases such as nephritis (JP-A 4-364171, etc.), and it is known that persistent hypotension action is manifested by inhibiting action of AII having strong vasoconstriction activity on an AII receptor.

In addition, it has been reported that an angiotensin II receptor (AT1 receptor) is involved in development and proliferation of cancer cells. (FEBS Letters 495(2001), 197-200; British Journal of Cancer, 1997, 75(9), 1279-1283; The Journal of Urology, vol. 151, 208-213, 1994; Cancer Letters 110 (1996)19-27).

However, there is no report suggesting that compounds having an AII antagonism exhibit effects of treating or preventing hormone-independent cancers, effects of inhibiting hormone-independent cancer cell proliferation and effects of inducing apoptosis of cancer cells.

In addition, WO99/44590 and WO01/60410 disclose sustained-release preparations containing benzimidazole derivatives having an AII antagonism. However, there is no description that the sustained-release preparations have effects of treating or preventing hormone-independent cancers, effects of inhibiting hormone-independent cancer cell proliferation, effects of inducing apoptosis of cancer cells and effects of treating or preventing cancers not requiring vascularization.

There are many cancer patients who do not respond to therapy by hormone drugs, and such cancer patients that proliferation of hormone-independent cancer cells is caused by use of hormone drugs, and effects of treatment of cancers by hormone drugs are not continued.

It is desired to develop anticancer agents which are excellent in effects of treating or preventing hormone-independent cancers or their metastasized lesions, or recurred cancers and have no side effects.

DISCLOSURE OF THE INVENTION

In view of the aforementioned circumstances, the present inventors intensively studied medicines having effects of treating or preventing hormone-independent cancers, or recurred cancers and, as a result, found that compounds having an angiotensin II antagonism or salts thereof competitively or non-competitively inhibit binding of angiotensin II to an angiotensin II receptor on a cancer cell membrane, block intracellular information due to a growth factor (e.g. EGF etc.), or inhibit action of an intracellular information transmitter protein such as STAT3 and MAP kinase, whereby, proliferation of cancer cells, in particular, hormone-independent cancer cells is inhibited and apoptosis is induced, therefore, those compounds or salts thereof are extremely effective for treating or preventing hormone-independent cancer cells or their cancer metastasized lesion or recurred cancers.

Proliferation of cancers is determined by balance between cell proliferation and apoptosis. Stimulation by a growth factor promotes proliferation of cells and inhibits apoptosis and, therefore, shifts this balance toward a proliferation side, and is very important to cancers. It is reported that a mechanism of a receptor for apoptosis inhibition by a growth factor relies on activation of intracellular apoptosis resistance factor Akt due to tyrosine kinase activity of a growth factor receptor. Therefore, if information outputted from a growth factor receptor can be blocked, cancer cells can be led apoptosis not only by inhibition of proliferation of cells but also by inhibition of activity of apoptosis inhibiting factor. Baced on these findings, the present inventors further studied, which resulted in completion of the present invention.

That is, the present invention relates to:

(1) A remedy or a preventive for hormone-independent cancer, which comprises a compound having an angiotensin II antagonism, its prodrug or a salt thereof;

(2) The agent according to the above (1), wherein the compound having an angiotensin II antagonism is a non-peptidic compound;

(3) The agent according to the above (1), wherein the compound having an angiotensin II antagonism is a compound having an oxygen atom in a molecule;

(4) The agent according to the above (1), wherein the compound having an angiotensin II antagonism is a compound having an ether linkage or a carbonyl group in a molecule;

(5) The agent according to the above (1), wherein the compound having an angiotensin II antagonism is a compound represented by the formula (I):

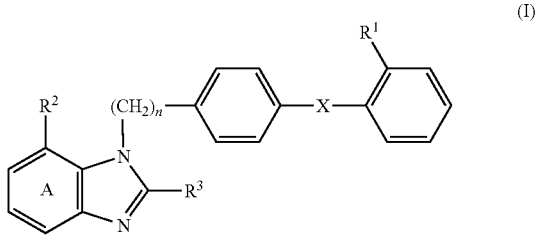

wherein $R^1$ denotes a group capable of forming an anion or a group which can be converted into said group, X denotes that a phenylene group and a phenyl group are bound directly or via spacer of 2 or less of atomic chains, n denotes 1 or 2, a ring A denotes a benzene ring optionally further substituted, $R^2$ denotes a group capable of forming an anion or a group which can be converted into said group, and $R^3$ denotes a hydrocarbon residue, which may be bound via a hetero atom and optionally substituted;

(6) The agent according to the above (1), wherein the compound having an angiotensin II antagonism or a salt thereof is Losartan, Losartan potassium, Eprosartan, Candesartan cilexetil, Candesartan, Valsartan, Telmisartan, Irbesartan, Olmesartan, Olmesartan medoxomil or Tasosartan;

(7) The agent according to the above (1), wherein the compound having an angiotensin II antagonism is 2-ethoxy-1-[[2'-(1H-tetrazol-5-yl)biphenyl-4-yl]methyl]benzimidazole-7-carboxylic acid;

(8) The agent according to the above (1), wherein the compound having an angiotensin II antagonism is 1-(cyclohexyloxycarbonyloxy)ethyl 2-ethoxy-1-[[2'-(1H-tetrazol-5-yl)biphenyl-4-yl]methyl]benzimidazole-7-carboxylate;

(9) The agent according to the above (1), wherein the compound having an angiotensin II antagonism is 2-ethoxy-1-[[2'-(2,5-dihydro-5-oxo-1,2,4-oxadiazol-3-yl)biphenyl-4-yl]methyl]benzimidazole-7-carboxylic acid;

(10) The agent according to the above (1), wherein the cancer is prostate cancer or breast cancer;

(11) The agent according to the above (1), wherein the cancer is hormone-independent cancer metastasized lesion of prostate cancer or breast cancer;

(12) A remedy or a preventive for hormone-independent cancer, which comprises a combination of a compound having an angiotensin II antagonism, its prodrug or a salt thereof, and a LH-RH agonist or antagonist;

(13) The agent according to the above (12), wherein the LH-RH agonist is leuprorelin or a salt thereof;

(14) A hormone-independent cancer cell proliferation inhibitor, which comprises a compound having an angiotensin II antagonism, its prodrug or a salt thereof;

(15) The agent according to the above (14), wherein the cancer cell is a cancer cell expressing an angiotensin II receptor;

(16) The agent according to the above (14), wherein the cancer is prostate cancer or breast cancer;

(17) A cancer cell apoptosis inducer, which comprises a compound having an angiotensin II antagonism, its prodrug or a salt thereof;

(18) The agent according to the above (17), wherein the cancer cell is a cancer cell expressing an angiotensin II receptor;

(19) The agent according to the above (17), wherein the cancer is prostate cancer or breast cancer;

(20) A remedy or a preventive for cancer not requiring vascularization, which comprises a compound having an angiotensin II antagonism, its prodrug or a salt thereof.

(21) The agent according to the above (20), wherein the cancer not requiring vascularization is metastasized cancer of prostate cancer or breast cancer;

(22) The agent according to the above (20), wherein the cancer is bone metastasized cancer;

(23) An agent for inhibiting intracellular signaling due to a cell growth factor, which comprises a compound having an angiotensin II antagonism, its prodrug or a salt thereof;

(24) A tyrosine phosphorylation inhibitor, which comprises a compound having an angiotensin II antagonism, its prodrug or a salt thereof;

(25) A method for treating or preventing hormone-independent cancer, which comprises administering an effective amount of a compound having an angiotensin II antagonism, its prodrug or a salt thereof to a mammal;

(26) A method for treating or preventing hormone-independent cancer, which comprises administering a combination of effective amounts of a compound having an angiotensin II antagonism, its prodrug or a salt thereof and a LH-RH agonist or antagonist to a mammal;

(27) A method for inhibiting hormone-independent cancer cell proliferation, which comprises administering an effective amount of a compound having an angiotensin II antagonism, its prodrug or a salt thereof to a mammal;

(28) A method for inducing cancer cell apoptosis, which comprises administering an effective amount of a compound having an angiotensin II antagonism, its prodrug or a salt thereof to a mammal;

(29) A method for treating or preventing cancer not requiring vascularization, which comprises administering an effective amount of a compound having an angiotensin II antagonism, its prodrug or a salt thereof to a mammal;

(30) A method for inhibiting intracellular signaling due to a cell growth factor, which comprises administering an effective amount of a compound having an angiotensin II antagonism, its prodrug or a salt thereof to a mammal;

(31) A method for inhibiting tyrosine phosphorylation, which comprises administering an effective amount of a compound having an angiotensin II antagonism, its prodrug or a salt thereof to a mammal;

(32) Use of a compound having an angiotensin II antagonism, its prodrug or a salt thereof for manufacturing a remedy or a preventive for hormone-independent cancer;

(33) Use of a compound having an angiotensin II antagonism, its prodrug or a salt thereof and a LH-RH agonist or antagonist for manufacturing a remedy or a preventive for hormone-independent cancer;

(34) Use of a compound having an angiotensin II antagonism, its prodrug or a salt thereof for manufacturing a hormone-independent cancer cell proliferation inhibitor;

(35) Use of a compound having an angiotensin II antagonism, its prodrug or a salt thereof for manufacturing a cancer cell apoptosis inducer;

(36) Use of a compound having an angiotensin II antagonism, its prodrug or a salt thereof for manufacturing a remedy or a preventive for cancer not requiring vascularization;

(37) Use of a compound having an angiotensin II antagonism, its prodrug or a salt thereof for manufacturing an agent for inhibiting intracellular signaling due to a cell growth factor;

(38) Use of a compound having an angiotensin II antagonism, its prodrug or a salt thereof for preparing a tyrosine phosphorylation inhibitor; and the like.

Further, the present invention relates to:

(39) a preventive or a remedy for recrudescent cancer, which comprises a compound having an angiotensin II antagonism, its prodrug or a salt thereof;

(40) the agent according to the above (39), wherein the recrudescent cancer is prostate cancer or breast cancer;

(41) a remedy or a preventive for recrudescent cancer, which comprises a combination of a compound having an angiotensin II antagonism, its prodrug or a salt thereof, and a LH-RH agonist or antagonist;

(42) the agent according to the above (41), wherein the LH-RH agonist is leuprorelin or a salt thereof;

(43) a method for preventing or treating recrudescent cancer, which comprises administering an effective amount of a compound having an angiotensin II antagonism, its prodrug or a salt thereof to a mammal;

(44) a method for preventing or treating recrudescent cancer, which comprises administering an effective amount of a compound having an angiotensin II antagonism, its prodrug or a salt thereof and a LH-RH agonist or antagonist to a mammal;

(45) use of a compound having an angiotensin II antagonism, its prodrug or a salt thereof for manufacturing a preventive or a remedy for recrudescent cancer;

(46) use of a compound having an angiotensin II antagonism, its prodrug or a salt thereof and a LH-RH agonist or antagonist for manufacturing a preventive or a remedy for recrudescent cancer; and the like.

BRIEF DESCRIPTION OF DRAWINGS

FIG. 10 shows a list of cases. "ope" denotes a patient who underwent prostate complete extirpation as initial therapy, and "RTx" indicates a patient who was undergoing radiation therapy by external irradiation as auxiliary therapy. The list shows a maximum and a minimum of a PSA value of a case (response (+)) in which reduction in a serum PSA value was observed among Bropress dosing.

Figure 1:
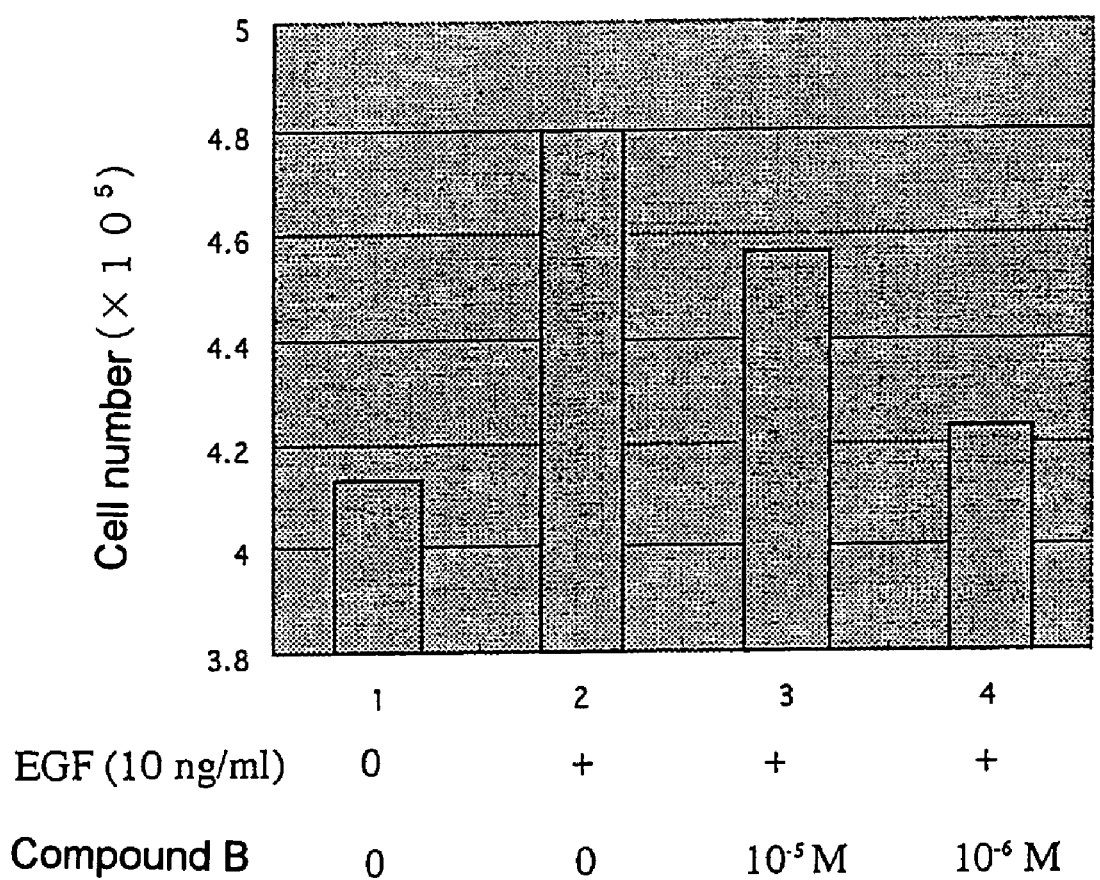
FIG. 1 shows the results of measurement of the cell number of DU145 cells in 5 days after addition of EGF and Compound B.

Hormone-dependent cancer means cancer which has a receptor for a hormone and in which a hormone is involved in development and proliferation of a tumor, such as prostate cancer, ovary cancer, cervical cancer, and breast cancer. Hormone therapy by administration of a hormone drug is frequently applied to a patient diagnosed as a positive hormone receptor.

On the other hand, hormone-independent cancer refers to cancer which does not respond to a hormone drug (e.g. cancer which is prostate cancer, ovary cancer, cervical cancer, breast cancer, but does not respond to a hormone drug) and cancer which has become not to respond to a hormone drug as a result of long term continuation of hormone therapy, in the aforementioned hormone-dependent cancer (e.g. cancer resistant to a LH-RH agonist such as leuprin, anti-androgen resistant cancer), including cancer which is recurred cancer of the aforementioned hormone-dependent cancer and has become not to respond to a hormone drug, and hormone-independent metastasized lesion such as prostate cancer and breast cancer (e.g. lymph node metastasis, marrow metastasis, and bone metastasized lesion of pelvis, bone, lumbar vertebrae and thoracic vertebrae which are derived from prostate cancer or breast cancer).

"Cancer" in the term "hormone-dependent cancer" and "hormone-independent cancer" means not only individual cancer cells but also a whole cancer tissue. However, in the present invention, "hormone-independent cancer" includes a cancer tissue and a cancer metastasized lesion at a transition stage from hormone dependency to hormone independency or at a growth stage of hormone-independent cancer cells. Further, hormone-independent cancer includes not only cancer accompanying vascularization and requiring this, but also cancer not requiring vascularization (e.g. hematopoietic metastasized tumor such as marrow metastasized cancer).

The angiotensin II antagonism in the present invention refers to action of competitively or non-competitively inhibiting binding of angiotensin II to an angiotensin II receptor on a cell membrane. It is known that compounds having such an angiotensin II antagonism alleviate strong vasoconstriction action and vessel smooth muscle proliferation action induced by angiotensin II, and ameliorate symptom of hypertension.

The compound having an angiotensin II antagonism used in the present invention may be peptidic or non-peptidic. For example, a non-peptidic compound having an antagonism which has an advantage of long acting time is preferable. As the compound having an angiotensin II antagonism, a compound having an oxygen atom in a molecule, inter alia, a compound having an ether linkage or a carbonyl group (the carbonyl may form a hydroxy group by resonance) is preferable, a compound having an ether linkage or a ketone derivative is more preferable, an ether derivative is particularly preferable.

As the non-peptidic compound having an angiotensin II antagonism, for example, JP-A 56-71073, JP-A 56-71074, JP-A 57-98270, JP-A 58-157768, U.S. Pat. No. 4,355,040 and U.S. Pat. No. 4,340,598 disclose imidazole derivatives, EP-253310, EP-291969, EP-324377, EP-403158, WO-910027, JP-A 63-23868 and JP-A 1-117876 disclose improved imidazole derivatives, U.S. Pat. No. 5,183,899, EP-323841, EP-409332 and JP-A 1-287071 disclose pyrrole, pyrazole and triazole derivatives, U.S. Pat. No. 4,880,804, EP-0392317, EP-0399732, EP-0400835, EP-425921, EP-459136 and JP-A 3-63264 disclose benzimidazole derivatives, EP-399731 discloses azaindene derivatives, EP-407342 discloses pyrimidone derivatives, EP-411766 discloses quinazoline derivatives, EP-430300 discloses xanthine derivatives, EP-434038 discloses fused imidazole derivatives, EP-442473 discloses pyrimidinedione derivatives, EP-443567 discloses thienopyridone derivatives, and EP-445811, EP-483683, EP-518033, EP-520423, EP-588299, and EP-603712 disclose heterocyclic compounds. Journal of Medicinal Chemistry, vol. 39, No. 3, pp 625-656, 1966 describes representative compounds among them. As the non-peptidic compound having an angiotensin II antagonism, any non-peptidic compounds having an angiotensin II antagonism may be used in addition to the aforementioned compounds described in known publications. Inter alia, Losartan (DuP753), Losartan potassium, Eprosartan (SK & F108566), Candesartan cilexetil (TCV-116), Valsartan (CGP-48933), Telmisartan (BIBR277), Irbesartan (SR47436), Tasosartan (ANA-756), Olmesartan medoxomil and metabolism active substances thereof (Candesartan, Olmesartan etc.) are preferably used.

In addition, as the non-peptidic compound having an angiotensin II antagonism, for example, a bendimidazole derivative represented by the formula (I):

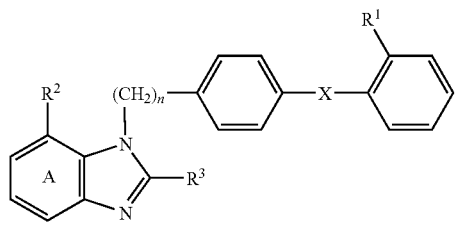

(I)

wherein $R^1$ denotes a group capable of forming an anion or a group which can be converted into said group, X denotes that a phenylene group and a phenyl group are bound directly or via a spacer of 2 or less atomic chains, n denotes an integer of 1 or 2, a ring A denotes a benzene ring optionally further substituted, $R^2$ denotes a group capable of forming an anion or a group which can be converted into said group, and $R^3$ denotes a hydrocarbon residue which may bind via a hetero atom and optionally substituted (preferably a hydrocarbon residue which may have substituted and binds via an oxygen atom), or a salt thereof is preferably used.

Examples of the group capable of forming an anion (a group having a hydrogen atom which can be released as a proton) as $R^1$ in the formula (I) include (1) a carboxyl group, (2) a tetrazolyl group, (3) a trifluoromethanesulfonic acid amido group (—NHSO$_2$CF$_3$), (4) a phosphoric acid group, (5) a sulfonic acid group, and (6) a 5 to 7-membered (preferably 5 to 6-membered) monocyclic optionally substituted heterocyclic residue containing one or two or more of N, S and O.

Examples of the "5 to 7-membered (preferably 5 to 6-membered) monocyclic optionally substituted heterocyclic residue containing one or two or more of N, S and O" include:

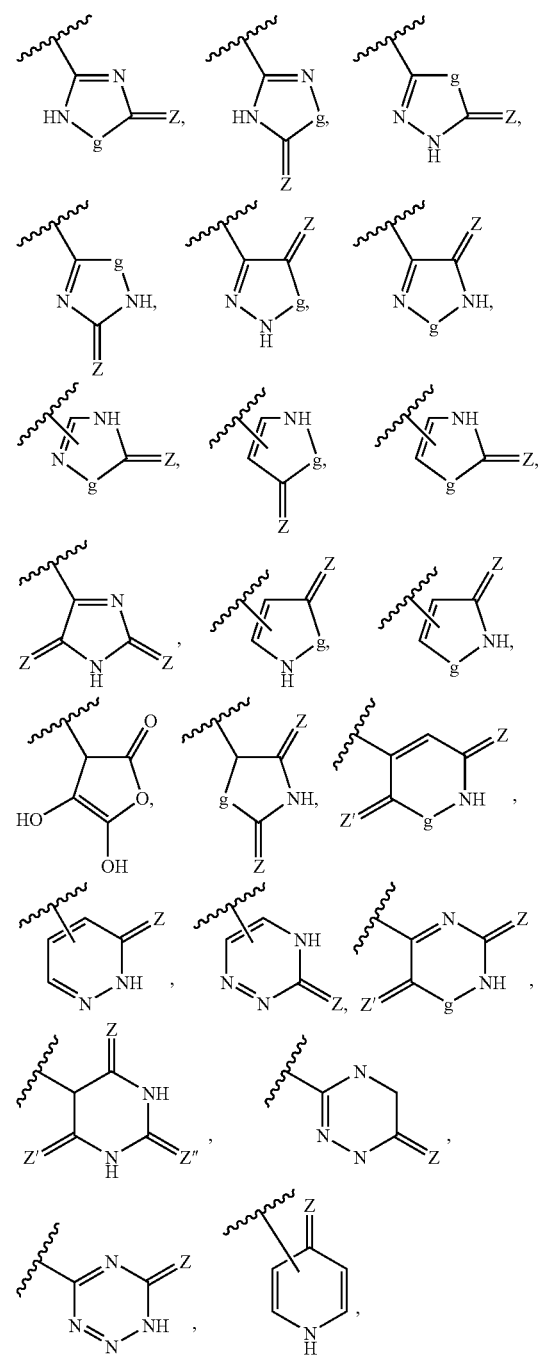

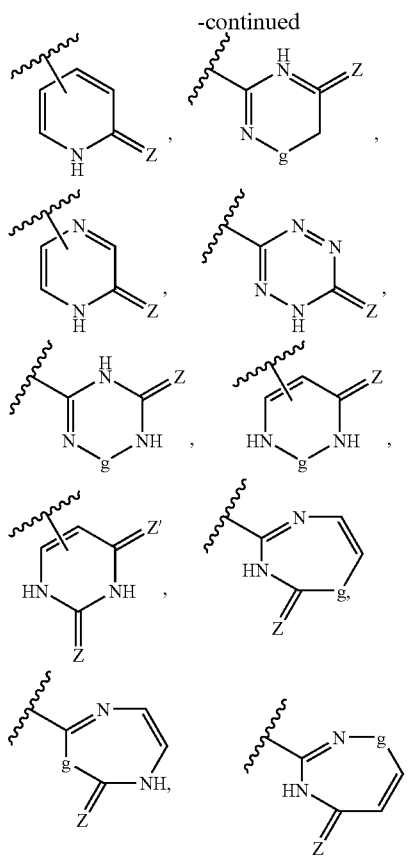

wherein binding between a heterocyclic residue represented by $R^1$ and a phenyl group to be bound with the heterocyclic residue may be via one of plural existing nitrogen atoms, in addition to the aforementioned carbon-carbon binding, when g indicates —NH— in the aforementioned formula. For example, when $R^1$ is represented by:

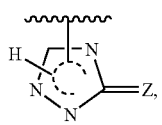

specifically, there are exemplified:

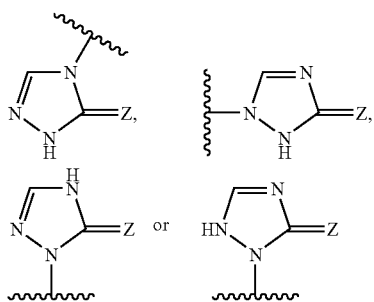

respectively. Other examples of binding via a nitrogen atom include:

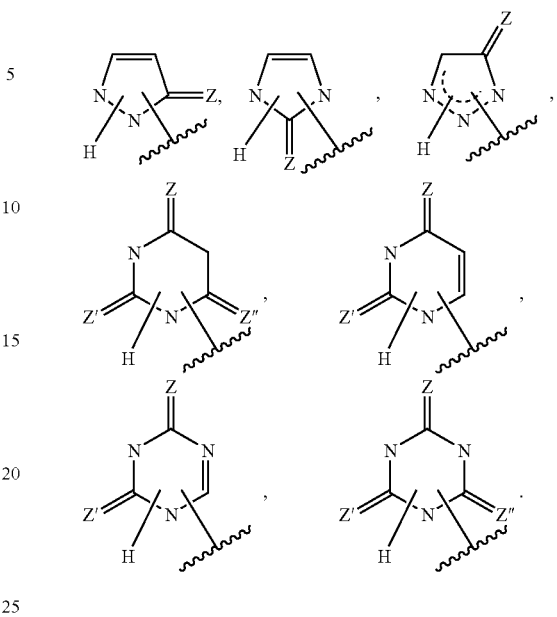

In the aforementioned formula, g denotes —CH$_2$—, —NH—, —O— or —S(O)$_m$—, >=Z, >=Z' and >=Z" denote a carbonyl group, a thiocarbonyl group or an optionally oxidized sulfur atom (e.g. S, S(O), S(O$_2$) etc.) (preferably a carbonyl or thiocarbonyl group, more preferably a carbonyl group), and m denotes an integer of 0, 1 or 2.

As the heterocyclic residue represented by $R^1$, for example, a group having a —NH— or —OH group as a proton donor, and a carbonyl group, a thiocarbonyl group or a sulfinyl group as a proton acceptor at the same time, such as an oxadiazolone ring, an oxadiazolothione ring and a thiadiazolone ring, is preferable. In the heterocyclic residue represented by $R^1$, cyclic substituents may bind to form a fused ring. As the heterocyclic residue represented by $R^1$, a 5 to 6-membered ring residue is preferable, and a 5-membered cyclic residue is more preferable.

As the heterocyclic residue represented by $R^1$, a group represented by the formula:

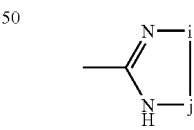

wherein i denotes —O— or —S—, j denotes >=O, >=S or >=S(O)$_m$, and m is as defined above (inter alia, 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl, particularly, 2,5-dihydro-5-oxo-1,2,4-oxathiazol-3-yl) is preferable.

The aforementioned heterocyclic residue ($R^1$) has the following tautomers. For example, when Z is O and g is O in

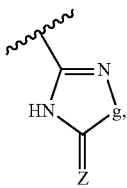

three tautomers such as the following a', b' and c' are present:

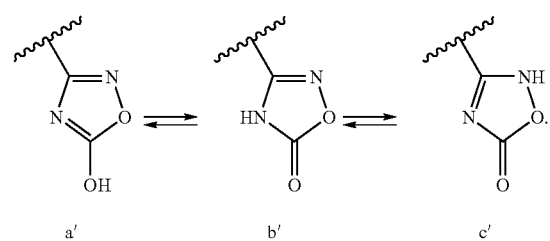

The heterocyclic residue represented by the formula:

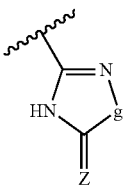

includes all of the aforementioned a', b' and c'.

The group capable of forming an anion as $R^1$ may be protected with an optionally substituted lower ($C_{1-4}$)alkyl group or acyl group (e.g. lower ($C_{2-5}$)alkanoyl, benzoyl etc.) at a replaceable position.

Examples of the optionally substituted lower ($C_{1-4}$)alkyl group include (1) a lower ($C_{1-4}$)alkyl group optionally substituted with 1 to 3 phenyl group(s) optionally substituted with a halogen atom, nitro, lower ($C_{1-4}$)alkyl, and lower ($C_{1-4}$) alkoxy (e.g. methyl, triphenylmethyl, p-methoxybenzyl, p-nitrobenzyl etc.), (2) a lower ($C_{1-4}$) alkoxy-lower ($C_{1-4}$)alkyl group (e.g. methoxymethyl ethoxymethyl etc.), and (3) a group represented by the formula —CH($R^4$)—OCOR$^5$ [wherein $R^4$ denotes (a) hydrogen, (b) a straight or branched lower alkyl group having 1 to 6 carbon atoms (e.g. methyl, ethyl, n-propyl, isopropyl, n-butyl, isobutyl, t-butyl, n-pentyl, isopentyl, neopentyl etc.), (c) a straight or branched lower alkenyl group having 2 to 6 carbon atoms or (d) a cycloalkyl group having 3 to 8 carbon atoms (e.g. cyclopentyl, cyclohexyl, cycloheptyl etc.), and $R^5$ denotes (a) a straight or branched lower alkyl group having 1 to 6 carbon atoms (e.g. methyl, ethyl, n-propyl, isopropyl, n-butyl, isobutyl, sec-butyl, t-butyl, n-pentyl, isopentyl, neopentyl etc.), (b) a straight or branched lower alkenyl group having 2 to 6 carbon atoms, (c) a lower alkyl group having 1 to 3 carbon atoms which is substituted with a cycloalkyl group having 3 to 8 carbon atoms (e.g. cyclopentyl, cyclohexyl, cycloheptyl etc.) or an optionally substituted aryl group (a phenyl or naphthyl group optionally substituted with a halogen atom, nitro, lower ($C_{1-4}$)alkyl, lower ($C_{1-4}$)alkoxy) (e.g. benzyl, p-chlorobenzyl, phenethyl, cyclopentylmethyl, cyclohexylmethyl etc.) (d) a lower alkenyl group having 2 to 3 carbon atoms which is substituted with cycloalkyl having 3 to 8 carbon atoms or an optionally substituted aryl group (e.g. a phenyl or naphthyl group optionally substituted with a halogen atom, nitro, lower ($C_{1-4}$)alkyl, lower ($C_{1-4}$)alkoxy) (e.g. the group having an alkenyl part such as vinyl, propenyl, allyl and isopropenyl, such as cinnamyl etc.), (e) an optionally substituted aryl group (e.g. a phenyl or naphthyl group optionally having halogen atom, nitro, lower ($C_{1-4}$)alkyl or lower ($C_{1-4}$)alkoxy, such as phenyl, p-tolyl, naphthyl etc.), (f) a straight or branched lower alkoxy group having 1 to 6 carbon atoms (e.g. methoxy, ethoxy, n-popoxy, isopropoxy, n-butoxy, isobutoxy, sec-butoxy, t-butoxy, n-pentyloxy, isopentyloxy, neopentyloxy etc.), (g) a straight or branched lower alkenyloxy group having 2 to 8 carbon atoms (e.g. allyloxy, isobutenyloxy etc.), (h) a cycloalkyloxy group having 3 to 8 carbon atoms (e.g. cyclopentyloxy, cyclohexyloxy, cyclopentyloxy etc.) (i) a lower alkoxy group having 1 to 3 carbon atoms which is substituted with a cycroalkyl group having 3 to 8 carbon atoms (e.g. cyclopentyl, cyclohexyl, cycloheptyl etc.) or an optionally substituted aryl group (e.g. a phenyl or naphthyl group optionally substituted with a halogen atom, nitro, lower ($C_{1-4}$)alkyl, lower ($C_{1-4}$)alkoxy etc.) (e.g. the group having an alkoxy part such as methoxy, ethoxy, n-propoxy and isopropoxy, such as benzyloxy, phenethyloxy, cyclopentylmethoxy and cyclohexylmethoxy), (j) a lower alkenyloxy group having 2 to 3 carbon atoms which is substituted with a cycloalkyl group having 3 to 8 carbon atoms (e.g. cyclopentyl, cyclohexyl, cycloheptyl etc.) or an optionally substituted aryl group (e.g. a phenyl or naphthyl group optionally substituted with a halogen atom, nitro, lower ($C_{1-4}$)alkyl, lower ($C_{1-4}$) alkoxy etc.) (e.g. the group having an alkenyloxy part such as vinyloxy, propenyloxy, allyloxy and isopropenyloxy, such as cinnamyloxy etc.) or (k) an optionally substituted aryloxy group (e.g. a phenoxy or naphthoxy group optionally substituted with a halogen atom, nitro, lower ($C_{1-4}$)alkyl or lower ($C_{1-4}$)alkoxy, such as phenoxy, p-nitrophenoxy, naphthoxy etc.)].

In addition, the group capable of forming an anion as $R^1$ may have a substituent such as an optionally substituted lower ($C_{1-4}$)alkyl group (examples thereof include the same "optionally substituted lower ($C_{1-4}$)alkyl groups" as those exemplified as a protecting group for the group capable of forming an anion as $R^1$), a halogen atom, nitro, cyano, lower ($C_{1-4}$)alkoxy, or amino optionally substituted with 1 or 2 lower ($C_{1-4}$)alkyl(s) at a replaceable position, in addition to the aforementioned protecting group such as an optionally substituted lower ($C_{1-4}$)alkyl group or acyl group (e.g. lower ($C_{2-5}$)alkanoyl, benzoyl etc.).

The group which can be converted into a group capable of forming an anion (group having a hydrogen atom which can be released as a proton) as $R^1$ in the aforementioned formula may be a group which can be converted into a group capable of forming an anion under biological, that is, physiological conditions (e.g. a reaction in a living body such as oxidation, reduction and hydrolysis by an enzyme in a living body) (so-called prodrug), or a group which can be converted into a group capable of forming an anion represented by $R^1$ by a chemical reaction (so-called synthetic intermediate), such as (1) a carboxyl group, (2) a tetrazolyl group, (3) a trifluoromethanesulfonic acid amido group (—NHSO$_2$CF$_3$), (4) a phosphoric acid group, (5) a sulfonic acid group, and (6) a 5 to 7-membered (preferably 5 to 6-membered) monocyclic optionally substituted heterocyclic residue containing one or more of N, S, and O, each being protected with cyano, a N-hydroxy carbamimidoyl group (—C(=N—OH)—NH$_2$), or an optionally substituted lower (C$_{1-4}$)alkyl group or acyl group.

As R$^1$, carboxyl, tetrazoryl or 2,5-dihydro-5-oxo-1,2,4-oxadiazol-3-yl (preferably tetrazolyl) or cyano, or N-hydroxycarbamimidoyl (preferably cyano), which may be protected with optionally substituted lower (C$_{1-4}$)alkyl (e.g. methyl, triphenylmethyl, methoxymethyl, ethoxymethyl, p-methoxybenzyl, p-nitrobenzyl etc.) or acyl group (e.g. lower (C$_{2-5}$)alkanoyl, benzoyl etc.) is preferable. Particularly, cyano is preferably used.

In the aforementioned formula, X denotes that adjacent phenylene group and phenyl group are bound directly or via a spacer of 2 or less atomic chains (preferably direct bond). As the spacer of 2 or less atomic chains, any divalent chains having the number of atoms constituting a straight part of 1 or 2 any be used, and those chains may have a side chain. Specific examples include lower (C$_{1-4}$)alkylene, —CO—, —O—, —S—, —NH—, —CO—NH—, —O—CH$_2$—, —S—CH$_2$—, and —CH=CH—, which have the number of atoms constituting a straight chain part of 1 or 2.

In the aforementioned formula, n denotes an integer of 1 or 2 (preferably 1).

In the aforementioned formula, a ring A denotes a banzene ring optionally further having a substituent in addition to a substituent R$^2$, and examples of the substituent include (1) halogen (e.g F, Cl, Br etc.), (2) cyano, (3) nitro, (4) optionally substituted lower (C$_{1-4}$)alkyl, (5) lower (C$_{1-4}$)alkoxy, (6) optionally substituted amino group (e.g. amino, N-lower (C$_{1-4}$)alkylamino (e.g. methylamino etc.), N,N-di-lower (C$_{1-4}$) alkylamino (e.g. dimethylamino etc.), N-arylamino (e.g. phenylamino etc.), alicyclic amino (e.g. morpholino, piperidino, piperazino, N-phenylpiperazino etc.) etc.), (7) a group represented by the formula —CO-D' [wherein D' denotes a hydroxy group, or lower (C$_{1-4}$)alkoxy in which an alkyl part may be substituted with hydroxy group, lower (C$_{1-4}$)alkoxy, lower (C$_{2-6}$)alkanyloxy (e.g. acetoxy, pivaloyloxy etc.), lower (C$_{1-6}$)alkoxycarbonyloxy (e.g. methoxycarbonyloxy, ethoxycarbonyloxy etc.) or lower (C$_{3-6}$)cycloalkoxycarbonyloxy (e.g. cyclohexyloxycarbonyloxy etc.)], or (8) a tetrazolyl, a trifluoromethanesulfonic acid amido group, a phosphoric acid group or a sulfonic acid group, each being optionally protected with optionally substituted lower (C$_{1-4}$) alkyl (examples include the same "optionally substituted lower (C$_{1-4}$)alkyl groups" as those exemplified as a protecting group for a group capable of forming an anion as R$^1$) or acyl group (e.g. lower (C$_{2-5}$)alkanoyl, benzoyl etc.).

These substituents may replace at 1 to 2 replaceable position(s) on a benzene ring at the same time. As a substituent which may be further possessed by a ring A in addition to a substituent R$^2$, optionally substituted lower (C$_{1-4}$)alkyl (e.g. lower (C$_{1-4}$)alkyl optionally substituted with a hydroxyl group, a carboxyl group or a halogen), and a halogen are preferable. It is more preferable that a ring A has not a substituent in addition to a substituent R$^2$.

In the above formula, examples of a group capable of forming an anion (a group having a hydrogen atom which can be released as a proton) as R$^2$ include (1) an optionally esterified or amidated carboxyl group, (2) a tetrazolyl group, (3) a trifluoromethanesulfonic acid amido group (—NHSO$_2$CF$_3$), (4) a phosphoric acid group, and (5) a sulfonic acid group. These groups may be protected with an optionally substituted lower alkyl group (examples include the same "optionally substituted lower (C$_{1-4}$)alkyl groups" as those exemplified as a protecting group for a group capable of forming an anion as R$^1$) or an acyl group (e.g. lower (C$_{2-5}$)alkanoyl, benzoyl etc.), and may be any groups as far as they are a group capable of forming an anion, or a group which can be converted into the group, under biological, that is, physiological conditions (e.g. a reaction in a living body such as oxidation, reduction and hydrolysis by an enzyme in a living body), or chemically.

Examples of the optionally esterified or amidated carboxyl as R$^2$ include a group represented by the formula —CO-D {wherein D denotes (1) a hydroxy group, (2) optionally substituted amino (e.g. amino, N-lower (C$_{1-4}$)alkylamino, N,N-di-lower (C$_{1-4}$)alkylamino etc.) or (3) optionally substituted alkoxy {e.g. (i) a lower (C$_{1-6}$)alkoxy group in which an alkyl part may be substituted with a hydroxy group, optionally substituted amino (e.g. amino, N-lower (C$_{1-4}$)alkylamino, N,N-di-lower (C$_{1-4}$)alkylamino, piperidino, morpholino etc.), halogen, lower (C$_{1-6}$)alkoxy, lower (C$_{1-6}$)alkylthio, lower (C$_{3-8}$)cycloalkoxy, or optionally substituted dioxolenyl (e.g. 5-methyl-2-oxo-1,3-dioxolen-4-yl etc.), or (ii) a group represented by the formula —O—CH(R$^6$)—OCOR$^7$ [wherein R$^6$ represents (a) hydrogen, (b) a straight or branched lower alkyl group having 1 to 6 carbon atoms (e.g. methyl, ethyl, n-propyl, isopropyl, n-butyl, isobutyl, t-butyl, n-pentyl, isopentyl, neopentyl etc.), (c) a straight or branched lower alkenyl group having 2 to 6 carbon atoms, or (d) a cycloalkyl group having 3 to 8 carbon atoms (e.g. cyclopentyl, cyclohexyl, cycloheptyl etc.), and R$^7$ denotes (a) a straight or branched lower alkyl group having 1 to 6 carbon atoms (e.g. methyl, ethyl, n-propyl, isopropyl, n-butyl, isobutyl, sec-butyl, t-butyl, n-pentyl, isopentyl, neopentyl etc.), (b) a straight or branched lower alkenyl group having 2 to 6 carbon atoms, (c) a lower alkyl group having 1 to 3 carbon atoms which is substituted with a cycloalkyl group having 3 to 8 carbon atoms (e.g. cyclopentyl, cyclohexyl, cycloheptyl etc.) or an optionally substituted aryl group (e.g. phenyl or naphthyl group optionally substituted with a halogen atom, nitro, lower (C$_{1-4}$)alkyl, lower (C$_{1-4}$)alkoxy etc.) (e.g. benzyl, p-chlorobenzyl, phenethyl, cyclopentylmethyl, cyclohexylmethyl etc.), (d) a lower alkenyl group having 2 to 3 carbon atoms which is substituted with cycloalkyl having 3 to 8 carbon atoms or an optionally substituted aryl group (e.g. phenyl or naphthyl group optionally substituted with a halogen atom, nitro, lower (C$_{1-4}$)alkyl, lower (C$_{1-4}$)alkoxy etc.) (e.g. the group having an alkenyl part such as vinyl, propenyl, allyl, isopropenyl etc., such as cinnamyl etc.), (e) an optionally substituted aryl group (e.g. phenyl or naphthyl group optionally substituted with a halogen atom, nitro, lower (C$_{1-4}$)alkyl, lower (C$_{1-4}$)alkoxy etc., such as phenyl, p-tolyl, naphthyl etc.), (f) a straight or branched lower alkoxy group having 1 to 6 carbon atoms (e.g. methoxy, ethoxy, n-propoxy, isopropoxy, n-butoxy, isobutoxy, sec-butoxy, t-butoxy, n-pentyloxy, isopentyloxy, neopentyloxy etc.), (g) a straight or branched lower alkenyloxy group having 2 to 8 carbon atoms (e.g. allyloxy, isobutenyloxy etc.), (h) a cycloalkyloxy group having 3 to 8 carbon atoms (e.g. cyclopentyloxy, cyclohexyloxy, cycloheptyloxy etc.), (i) a lower alkoxy group having 1 to 3 carbon atoms which is substituted with cycloalkyl having 3 to 8 carbon atoms (e.g. cyclopentyl, cyclohexyl, cycloheptyl etc.) or an optionally substituted aryl group (e.g. phenyl or naphthyl group optionally substituted with a halogen atom, nitro, lower (C$_{1-4}$)alkyl, lower (C$_{1-4}$)alkoxy etc.) (e.g. the group having an alkoxy part such as methoxy, ethoxy, n-propoxy, isopropoxy etc. such as benzyloxy, phenethyloxy, cyclopentylmethoxy, cyclohexylmethoxy etc.), (j) a lower alkenyloxy having 2 to 3 carbon atoms substituted with cycloalkyl having 3 to 8 carbon atoms (e.g. cyclopentyl, cyclohexyl, cycloheptyl etc.) or an optionally substituted aryl group (e.g. phenyl or naphthyl group optionally substituted with a halogen atom, nitro, lower (C$_{1-4}$)alkyl, lower (C$_{1-4}$) alkoxy etc.) (e.g. the group having an alkenyloxy part such as vinyloxy, propenyloxy, allyloxy, isopropenyloxy etc.), such as cinnamyl oxy etc) or (k) an optionally substituted aryloxy group (e.g. phenoxy or naphthoxy group optionally substituted with a halogen atom, nitro, lower ($C_{1-4}$)alkyl, lower ($C_{1-4}$)alkoxy etc.), such as phenoxy, p-nitrophenoxy, naphthoxy etc.)]}.

As $R^2$, optionally esterified carboxyl is preferable. Specific examples thereof include —COOH and a salt thereof, —COOMe, —COOEt, —COOtBu, —COOPr, pivaloyloxymethoxycarbonyl, 1-(cyclohexyloxycarbonyloxy) ethoxycarbonyl, 5-methyl-2-oxo-1,3-dioxolen-4-yl-methoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, and cyclopentylcarbonyloxymethoxycarbonyl, and may be any groups as far as they are a group capable of forming an anion (e.g. COO⁻, a derivative thereof etc.), or a group which can be converted into the group, under biological, that is, physiological conditions (e.g. a reaction in a living body such as oxidation, reduction and hydrolysis by an enzyme in a living body), or chemically, or a carboxyl group, or a prodrug thereof.

As the aforementioned $R^2$, a group represented by the formula —CO-D [wherein D denotes (1) a hydroxy group, or (2) lower ($C_{1-4}$)alkoxy in which an alkyl part may be substituted with a hydroxy group, amino, halogen, lower ($C_{2-6}$) alkanoyloxy (e.g. acetoxy, pivaloyloxy etc.), lower ($C_{3-8}$) cycloalkanoyloxy, lower ($C_{1-6}$)alkoxycarbonyloxy (e.g. methoxycarbonyloxy, ethoxycarbonyloxy etc.), lower ($C_{3-8}$) cycloalkoxycarbonyloxy (e.g. cyclohexyloxycarbonyloxy etc.), lower ($C_{1-4}$)alkoxy or lower ($C_{3-8}$)cycloalkoxy] is preferable and, inter alia, carboxyl esterified with lower ($C_{1-4}$) alkyl (preferably methyl or ethyl) is preferable.

In the above formula, examples of the "hydrocarbon residue" in the "hydrocarbon residue which may bind via a hetero atom and optionally substituted" represented by $R^3$ include (1) an alkyl group, (2) an alkenyl group, (3) an alkynyl group, (4) a cycloalkyl group, (5) an aryl group, and (6) an aralkyl group and, inter alia, an alkyl group, an alkenyl group and a cycloalkyl group are preferable.

The aforementioned (1)alkyl group may be a straight or branched lower alkyl group having about 1 to 8 carbon atoms, and examples thereof include methyl, ethyl, propyl, isopropyl, butyl, isobutyl, sec-butyl, t-butyl, pentyl, i-pentyl, hexyl, heptyl and octyl.

The aforementioned (2) alkenyl group may be a straight or branched lower alkenyl group having about 2 to 8 carbon atoms, and examples include vinyl, propenyl, 2-butenyl, 3-butenyl, isobutenyl, and 2-octenyl.

The aforementioned (3) alkynyl group may be a straight or branched lower alkynyl group having about 2 to 8 carbon atoms, and examples include ethynyl, 2-propynyl, 2-butynyl, 2-pentynyl, and 2-octynyl.

The aforementioned (4) cycloalkyl group may be lower cycloalkyl having about 3 to 6 carbon atoms, and examples include cyclopropyl, cyclobutyl, cyclopentyl, and cyclohexyl.

The aforementioned alkyl group, alkenyl group, alkynyl group or cycloalkyl group may be substituted with a hydroxy group, an optionally substituted amino group (e.g. amino, N-lower ($C_{1-4}$)alkylamino, N,N-di-lower ($C_{1-4}$)alkylamino etc.), a halogen, a lower ($C_{1-4}$)alkoxy group, or a lower ($C_{1-4}$)alkylthio group.

Examples of the aforementioned (5) aralkyl group include phenyl-lower ($C_{1-4}$)alkyl such as benzyl and phenethyl, and examples of the aforementioned (6) aryl group include phenyl.

The aforementioned aralkyl group or aryl group may have, for example, halogen (e.g. F, Cl, Br etc.), nitro, optionally substituted amino group (e.g. amino, N-lower ($C_{1-4}$)alkylamino, N,N-di-lower ($C_{1-4}$)alkylamino etc.), lower ($C_{1-4}$) alkoxy (e.g. methoxy, ethoxy etc.), lower ($C_{1-4}$)alkylthio (e.g. methylthio, ethylthio etc.), or lower ($C_{1-4}$)alkyl (e.g. methyl, ethyl etc.) at an arbitrary position on a benzene ring thereof.

Among the above groups, as the "hydrocarbon residue" in the "hydrocarbon residue which may bind via a hetero atom and optionally substituted" represented by $R^3$, an optionally substituted alkyl or alkenyl group (e.g. a lower ($C_{1-5}$)alkyl or lower ($C_{2-5}$)alkenyl group optionally substituted with a hydroxy group, an amino group, halogen or a lower ($C_{1-4}$) alkoxy group etc.) is preferable and, inter alia, lower ($C_{1-5}$) alkyl (more preferable ethyl) is preferable.

Examples of the "hetero atom" in the "hydrocarbon residue which may bind via a hetero atom and optionally substituted" represented by $R^3$ include —O—, —S(O)$_m$— [m represents an integer of 0 to 2], and —NR'— [R' represents a hydrogen atom or lower ($C_{1-4}$)alkyl] and, inter alia, —O— is preferably used.

Among the above groups, as $R^3$, a lower ($C_{1-5}$)alkyl or lower ($C_{2-5}$)alkenyl group which may bind via —O—, —S(O)$_m$— [m represents an integer of 0 to 2] or —NR'— [R' represents hydrogen atom or lower ($C_{1-4}$)alkyl] and may be substituted with a substituent selected from a hydroxy group, an amino group, a halogen and a lower ($C_{1-4}$)alkoxy group is preferable and, inter alia, lower ($C_{1-5}$)alkyl or lower ($C_{1-5}$) alkoxy (more preferably ethoxy) is preferable.

Among the compounds having an angiotensin II antagonism represented by the formula (I), a benzimidazole-7-carboxylic acid derivative represented by the formula (I'):

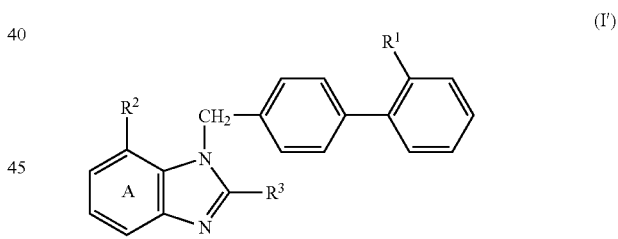

(I')

wherein R' denotes (1) a carboxyl group, (2) a tetrazolyl group or (3) a group represented by the formula:

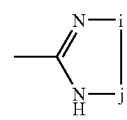

[wherein i denotes —O— or —S—, j denotes >=O, >=S or >=S(O)$_m$, and m is as defined above], a ring A denotes a benzene ring optionally substituted with lower ($C_{1-4}$)alkyl optionally substituted with a substituent other than a substituent $R^2$ (e.g. lower ($C_{1-4}$)alkyl optionally substituted with hydroxy group, carboxyl group, halogen etc.) or a halogen (preferably a benzene ring having no substituent other than a substituent $R^2$), $R^2$ denotes a group represented by the formula —CO-D [wherein D denotes (1) a hydroxy group or (2) lower ($C_{1-4}$)alkoxy in which an alkyl part may be substituted with a hydroxy group, amino, halogen, lower ($C_{2-6}$) alkanoyloxy (e.g. acetoxy, pivaloyloxy etc.), lower ($C_{3-8}$)cycloalkanoyloxy, lower ($C_{1-6}$)alkoxycarbonyloxy (e.g. methoxycarbonyloxy, ethoxycarbonyloxy etc.), lower ($C_{3-8}$)cycloalkoxycarbonyloxy (e.g. cyclohexyloxycarbonyloxy etc.), lower ($C_{1-4}$)alkoxy or lower ($C_{3-8}$) cycloalkoxy, and $R^3$ denotes a lower ($C_{1-5}$)alkyl or lower ($C_{2-5}$)alkenyl group (preferably lower ($C_{1-5}$)alkyl or lower ($C_{1-5}$)alkoxy; more preferably ethoxy) which may bind via —O—, —S(O)$_m$— [m represents an integer of 0 to 2] or —NR'— [R' represents hydrogen atom or lower ($C_{1-4}$)alkyl] and may be substituted with a substituent selected from a hydroxy group, an amino group, a halogen and a lower ($C_{1-4}$)alkoxy group] or a pharmacologically acceptable salt thereof is preferable. Inter alia, 2-ethoxy-1-[[2'-(1H-tetrazol-5-yl)biphenyl-4-yl]methyl]benzimidazole-7-carboxylic acid [Candesartan], 1-(cyclohexyloxycarbonyloxy)ethyl 2-ethoxy-1-[[2'-(1H-tetrazol-5-yl)biphenyl-4-yl]methyl] benzimidazole-7-carboxylate [Candesartan cilexetil], pivaloyloxymethyl 2-ethoxy-1-[[2'-(1H-tetrazol-5-yl)biphenyl-4-yl]methyl]benzimidazole-7-carboxylate, and 2-ethoxy-1-[[2'-(2,5-dihydro-5-oxo-1,2,4-oxadiazol-3-yl)biphenyl-4-yl] methyl]benzimidazole-7-carboxylic acid or salts thereof are preferable.

The aforementioned benzimidazole derivatives can be synthesized by a known method described, for example, in EP-425921, EP-459136, EP-553879, EP-578125, EP-520423, and EP-668272 or a similar method. When Candesartan cilaxetil is used, it is desired to use a stable C-type crystal described in EP-459136.

The compound having an angiotensin II antagonism used in the present invention or a prodrug thereof may be itself, or a pharmacologically acceptable salt. When the compound having an angiotensin II antagonism has an acidic group such as a carboxyl group and the like, examples of such a salt include salts with inorganic bases (e.g. alkali metal such as sodium, potassium etc., alkaline earth metal such as calcium, magnesium etc., and transition metal such as zinc, iron, copper etc.) or organic bases (e.g. organic amines such as trimethylamine, triethylamine, pyridine, picoline, ethanolamine, diethanoamine, triethanoamine, dicyclohexylamine, and N,N'-dibenzylethylenediamine, and basic amino acids such as arginine, lysine, and ornithine).

When the compound having an angiotensin II antagonism has a basic group such as an amino group, examples of the salt include salts with inorganic acids or organic acids (e.g. hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.), or acidic amino acids such as aspartic acid and glutamic acid.

A prodrug of the compound having an angiotensin II antagonism used in the present invention [hereinafter, referred to as AII antagonistic compound in some cases] refers to a compound which is converted into an AII antagonistic compound by a reaction with an enzyme, gastric acid or the like under physiological conditions in a living body, that is, a compound which is changed into an AII antagonistic compound by enzymatic oxidation, reduction, hydrolysis or the like, or a compound which is changed into an AII antagonistic compound by hydrolysis with gastric acid or the like. Examples of the prodrug of the AII antagonistic compound include compounds in which an amino group of the AII antagonistic compound is acylated, alkylated or phosphorylated (e.g. compounds in which an amino group of the AII antagonistic compound is eicosanoylated, alanylated, pentylaminocarbonized, (5-methyl-2-oxo-1,3-dioxolen-4-yl) methoxycarbonized, tetrahydrofuranylated, pyrrolidylmethylated, pivaloyloxymethylated, or tert-butylated); compounds in which a hydroxy group of the AII antagonistic compound is acylated, alkylated, phosphorylated or borated (e.g. compounds in which a hydroxy group of the AII antagonistic compound is acetylated, palmitoylated, propanoylated, pivaloylated, succinylated, fumarylated, alanylated or dimethylaminomethylcarbonized); compounds in which a carboxyl group of the AII antagonistic compound is esterized or amidated (e.g. compounds in which a carboxyl group of the AII antagonistic compound is ethylesterized, phenylesterized, carboxymethylesterized, dimethylaminomethylesterized, pivaloyloxymethylesterized, ethoxycarbonyloxyethylesterized, phthalidylesterized, (5-methyl-2-oxo-1,3-dioxolen-4-yl)methylesterized, cyclohexyloxycarbonylethylesterized, or methylamidated); and the like. These compounds can be prepared from the AII antagonistic compound by a known per se method.

Alternatively, the prodrug of the AII antagonistic compound may be compounds which are changed into the AII antagonistic compound under physiological conditions, such as those described in "Development of Medicaments", vol. 7, Molecular Design, pp. 163-198, published by Hirokawashoten in 1990.

In addition, the AII antagonistic compound may be a hydrate or a non-hydrate.

The compound having an angiotensin II antagonism, its prodrug or a pharmaceutically acceptable salt thereof can inhibit intracellular signaling by MAP kinase STAT3 which plays a central role in information transmission of a cell growth factor (e.g. EGF etc.) and cell proliferation, and can inhibit tyrosine phosphorylation of an intracellular protein. Further, the compound having an angiotensin II antagonism, its prodrug or a pharmaceutically acceptable salt has low toxicity. Therefore, it can be used to a mammal (e.g. human being, mouse, rat, rabbit, dog, cat, cow, pig, monkey etc.) as it is, or by mixing with a pharmaceutically acceptable carrier to formulate into a pharmaceutical composition, as an anticancer agent such as a remedy or a preventive for hormone-independent cancer, a hormone-independent cancer cell proliferation inhibitor, a cancer cell apoptosis inducer, a remedy or a preventive for not only cancer accompanied with vascuralization and requiring this, but also cancer not requiring vascuralization (e.g. hematopoietic metastasized tumor such as marrow metastasized cancer), and a remedy or a preventive for recurred cancer (in particular, recurred cancer of hormone-independent cancer which has become not to respond to a hormone drug).

Herein, as a pharmacologically acceptable carrier, various organic or inorganic carrier substances which are conventional as a pharmaceutical material are used. These substances are incorporated as an excipient, a lubricant, a binder or a disintegrating agent in a solid preparation; or as a solvent, a solubilizer, a suspending agent, an isotonic, a buffer or a soothing agent in a liquid preparation. If necessary, additives such as an antiseptic, an antioxidant, a coloring agent and a sweetener may be used.

Preferable examples of the excipient include lactose, white sugar, D-mannitol, D-sorbitol, starch, α starch, dextrin, crystalline cellulose, low substituted hydroxyprophylcellulose, sodium carboxymethylcellulose, gum arabic, dextrin, pullulan, light silicic acid anhydride, synthetic aluminum silisate, and magnesium aluminate methasilicate.

Preferable examples of the lubricant include magnesium stearate, calcium stearate, talc and colloidal silica.

Preferable examples of the binder include α starch, sucrose, gelatin, gum arabic, methylcellulose, carboxymethylcellulose, sodium carboxymethylcellulose, crystalline cellulose, white sugar, D-mannitol, trehalose, dextrin, pullulan, hydroxypropylcellulose, hydroxypropylmethylcellulose, and polyvinylpyrrolidone.

Preferable examples of the disintegrating agent include lactose, white sugar, starch, carboxymethylcellulose, calcium carboxymethylcellulose, sodium crosscarmerose, sodium carboxymethylstarch, light silicic acid anhydride, and low substituted hydroxypropylcellulose.

Preferable example of the solvent include water for injection, physiological saline, Ringer's solution, alcohol, propylene glycol, polyethlene glycol, sesame oil, corn oil, olive oil, and cotton seed oil.

Preferable examples of the solubilizer include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferable examples of the suspending agent include surfactants such as stearyltriethanolamine, sodium laurylsulfate, laurylaminopropionic acid, lecithin, benzalkonium chloride, benzethonium chloride, and monostearic acid glycerin; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose; polysorbates, and polyoxyethylene hydrogenated castor oil.

Preferable examples of the isotonic include sodium chloride, glycerin, D-mannitol, D-sorbitol, and glucose.

Preferable examples of the buffer include buffers of phosphate, acetate, carbonate and citrate.

Preferable examples of the soothing agent include benzyl alcohol.

Preferable examples of the antiseptic include paraoxybenzoic acid ethers, chlorobutanol, benzyl alcohol, phenethyl alcohol, dehydroacetic acid, and sorbic acid.

Preferable examples of the antioxidant include sulfite and ascorbate.

Preferable examples of the coloring agent include water-soluble edible tar dyes (e.g. edible dyes such as edible red No. 2 and No. 3, edible yellow No. 4 and No. 5, and edible blue No. 1 and No. 2), water-insoluble lake dyes (e.g. aluminum salts of the aforementioned water-soluble edible tar dyes), and natural dyes (e.g. β-carotin, chlorophyll, bengala).

Preferable examples of the sweetener include saccharin sodium, diposassium glycyrrhizinate, aspartame, and stevia.

Examples of a dosage form of a pharmaceutical composition include oral preparations such as tablets, capsules (including soft capsules and microcapsules), granules, powders, syrups, emulsions and suspensions; and parenteral preparations such as injectable preparations (e.g. subcutaneous injectable preparations, intravenous injectable preparations, intramuscular injectable preparations, intraperitoneal injectable preparations, and intravitreous injectable preparations), eyedrops, external preparations (e.g. nasal preparations, transdarmal preparations, ointments), suppositories (e.g. rectal suppositories, vagina suppositories), pellets, drops, and sustained-release preparations. These can be safely administered orally or parenterally.

A pharmaceutical composition can be prepared by conventional methods in pharmaceutical technique field, for example, the methods described in Japanese Pharmacopoeia. Hereinafter, specific methods for preparing preparations will be illustrated in detail.

For example, oral preparations are prepared by adding an excipient (e.g. lactose, white sugar, starch, D-mannitol etc.), a disintegrating agent (e.g. potassium carboxymethylcellulose etc.), a binder (e.g. α starch, gum arabic, carboxymethylcellulose, hydroxypropylcellulose, polyvinylpyrrolidone etc.) or a lubricant (e.g. talc, magnesium stearate, polyethylene glycol 6000 etc.) to an active ingredient, subjecting the mixture to compression molding, and then, if necessary, coating with a coating base by a known per se method for the purpose of taste masking, enteric properties or long lasting properties.

Examples of the coating base include sugar coating bases, water-soluble film coating bases, enteric film coating bases, and sustained release film coating bases.

As the sugar coating base, white sugar is used and, further, one or more kinds selected from talc, precipitated calcium carbonate, gelatin, gum arabic, Pullune, carnauba wax, etc. may be used in combination.

Examples of the water-soluble film coating base include cellulose polymers such as hydroxypropylcellulose, hydroxypropylmethylcellulose, hydroxyethylcellulose, and methylhydroxyethylcellulose; synthetic polymers such as polyvinylacetaldiethylaminoacetate, aminoalkylmethacrylate copolymer E [Eudragit E (trade name), Rohmpharma], and polyvinylpyrrolidone; polysaccharides such as pullulan.

Examples of the enteric film coating base include cellulose polymers such as hydroxypropylmethylcellulose phathalate, hydroxypropylmethylcellulose acetate succinate, carboxymethylethylcellulose, and cellulose acetate phathalate; acrylate polymers such as methacrylic acid copolymer L [Eudragit L (trade name), Rohmpharma], methacrylic acid copolymer LD [Eudragit L-30D55 (trade name), Rormpharma], and methacrylic acid copolymer S [Eudragit S (trade name), Rormpharma]; natural substances such as shellac.

Examples of the sustained-release film coating base include cellulose polymers such as ethylcellulose; and acrylate polymers such as aminoalkyl methacrylate copolymer RS [Eudragit RS (trade name), Rormpharma], and ethyl acrylate/methyl methacrylate copolymer suspension [Eudragit NE (trade name), Rormpharma].

The aforementioned coating bases may be used by mixing two or more of them at an appropriate ratio. Upon coating, light screens such as titanium oxide and diiron trioxide may be used.

Injectable preparations are prepared by dissolving, suspending or emulsifying an active ingredient in an aqueous solvent (e.g. distilled water, physiological saline, Ringer's solution etc.) or in an oily solvent (e.g. vegetable oil such as olive oil, sesame oil, cotton seed oil, and corn oil, propylene glycol etc.), together with a dispersing agent (e.g. Polysorbate 80, polyoxyethylene hydrogenated castor oil 60 etc.), polyethylene glycol, carboxymethylcellulose, sodium alginate etc.), a preservative (e.g. methylparaben, propylparaben, benzyl alcohol, chlorobutanol, phenol etc.), and an isotonic (e.g. sodium chloride, glycerol, D-mannitol, D-sorbitol, glucose etc.). At this time, if necessary, additives such as a solubilizer (e.g. sodium salicylate, sodium acetate etc.), a stabilizing agent (e.g. human serum albumin etc.), and a soothing agent (e.g. benzyl alcohol etc.) may be used.

Further, the compound having an angiotensin II antagonism, its prodrug or a pharmaceutically acceptable salt thereof together with a biodegradable polymer may be applied to a remedy or a preventive as a sustained-release preparation for hormone-independent cancer, a hormone-independent cancer cell proliferation inhibitor, a cancer cell apoptosis inducer, a remedy or a preventive for not only cancer accompanying vascuralization and requiring this, but also cancer not requiring vascuralization (e.g. hemapoietic metastasized tumor such as marrow metastasized cancer), and a remedy or a preventive for recurred or recrudescent cancer. Such a sustained-release preparation can be prepared by a known per se method.

Examples of such a sustained-release preparation include:

[1] a sustained-release preparation comprising the compound represented by the formula (I) or a salt thereof, and a biodegradable polymer,

[2] the sustained-release preparation described in [1], wherein the biodegradable polymer is an α-hydroxycarboxylic acid polymer,

[3] the sustained-release preparation described in [1], wherein the α-hydroxycarboxylic acid polymer is a lactic acid-glycolic acid polymer,

[4] the sustained-release preparation described in [3], wherein a molar ratio of lactic acid and glycolic acid is 100/0 to 40/60,

[5] the sustained-release preparation described in [2], wherein a weight average molecular weight of the polymer is 3,000 to 50,000,

[6] the sustained-release preparation described in [1], which is for injection,

[7] the sustained-release preparation described in [1], which contains a polyvalent metal,

[8] the sustained-release preparation described in [7], wherein the polyvalent metal is zinc, or

[9] a sustained-release preparation, which comprises the compound represented by the formula (I) or a salt thereof, a biodegradable polymer and a polyvalent metal.

Such sustained-release preparations are prepared and used according to the method described in WO99/44590.

Examples of another aspect of sustained-release preparations include:

[1] a sustained-release preparation, which comprises the compound represented by the formula (I) or a salt thereof, an ingredient obtained by treating a water-poorly soluble polyvalent metal compound with water, and a biodegradable polymer,

[2] the sustained-release preparation described in [1], wherein the biodegradable polymer is an α-hydroxycarboxylic acid polymer,

[3] the sustained-release preparation described in [2], wherein the α-hydroxycarboxylic acid polymer is a lactic acid-glycolic acid polymer,

[4] the sustained-release preparation described in [3], wherein a molar ratio of lactic acid and glycolic acid is 100/0 to 40/60,

[5] the sustained-release preparation described in [2], wherein a weight average molecular weight of a polymer is 3,000 to 50,000,

[6] the sustained-release preparation described in [1], which is for injection,

[7] the sustained-release preparation described in [1], wherein the polyvalent metal is zinc,

[8] the sustained-release preparation described in [1], wherein the polyvalent metal compound is zinc oxide,

[9] the sustained-release preparation described in [1], which further contains a polyvalent metal, and

[10] the sustained-release preparation described in [9], wherein the polyvalent metal is zinc.

Such sustained-release preparations are prepared and used according to the method described in WO 01/60410.

The dosage of the compound having an angiotensin II antagonism, its prodrug or a pharmaceutically acceptable salt thereof varies depending on the subject, the administration route, the symptom of disease. For example, when orally administered to a mammal, in particular, an adult (weight 50 kg), the compound having an angiotensin II antagonism, its prodrug or a pharmaceutically acceptable salt thereof as an active ingredient is usually administered at a dosage of about 0.001 to 500 mg, preferably 0.1 to 100 mg, and this dosage is desirably administered once to three times per day.

The sustained-release preparation of the present invention can be, used as such, or can be used as a raw material for formulating into various dosage forms, and can be administered as injectable preparations or implants to an intramuscular site, a subcutaneous site or an organ, transmucosal preparations to nasal cavity, rectum or uterus, or oral preparations (e.g. solid preparations such as capsules (e.g. hard capsules, soft capsules etc.), granules, and powders, and liquid preparations such as syrups, emulsions, and suspensions). The sustained-release preparation can be also administered by a needleless injector.

For example, in order to formulate the sustained-release preparation of the present invention into injectable preparations, it and a dispersing agent (e.g. surfactants such as Tween 80, and HCO-60, and polysaccharides such as sodium hyaluronate, carboxymethylcellulose, and sodium aliginate), a preservative (e.g. methylparaben, propylparaben etc.), and an isotonic (e.g. sodium chloride, mannitol, sorbitol, glucose, proline etc.) can be formulated into an aqueous suspension, or it and a vegetable oil such as sesame oil and corn oil can be dispersed into an oily suspension, to obtain a sustained-release injectable preparation which can be actually used.

A particle diameter of the sustained-release preparation of the present invention is in a range satisfying dispersity and needle penetrating properties when used as an injectable suspension. For example, an average particle diameter is in a range of about 0.1 to 300 μm, preferably about 0.5 to 150 μm, more preferably about 1 to 100 μm.

Examples of a method of formulating the sustained-release preparation of the present invention into a sterile preparation include sterilization of entire manufacturing steps, sterilization with gamma-ray, and addition of an antiseptic, being not particularly limited.

Since the sustained-release preparation of the present invention has low toxicity, it can be used as a safe medicament to a mammal (e.g. human being, cow, pig, dog, cat, mouse, rat, rabbit etc.).

Although the dosage of the sustained-release preparation of the present invention varies depending on the kind and content of the compound having an AII antagonism which is a primary drug, the dosage form, the release lasting time of the compound having an AII antagonism, the symptom of disease, and the subject animal, it may be an effective amount of the compound having an AII antagonism. For example, when the sustained-release preparation is a one month preparation, the dosage of the compound having an AII antagonism can be appropriately selected from the range of preferably about 0.01 mg to 10 mg/kg weight, more preferably about 0.05 mg to 5 mg/kg weight per adult.

The dosage of the sustained-release preparation can be appropriately selected from the range of preferably about 0.05 mg to 50 mg/kg weight, more preferably about 0.1 mg to 30 mg/kg weight per adult.

This dosage can be administered, for example, once in several weeks, once in a month or once in several months (e.g. three months, four months, six months etc.), and can be appropriately selected according to the kind and content of the compound having an AII antagonism which is a primary drug, the dosage form, the release lasting time of the compound having an AII antagonism, the symptom of disease, and the subject animal.

The sustained-release preparation of the present invention can be advantageously used as an anticancer agent such as a remedy or a preventive for hormone-independent cancer, a hormone-independent cancer cell proliferation inhibitor, a cancer cell apoptosis inducer, a remedy or a preventive for not only cancer accompanying vascularization and requiring this, but also cancer not requiring vascularization, and a remedy or a preventive for recurred or recrudescent cancer, and can maintain the constant blood concentration regardless of day or night, therefore, the dosage and dosing frequency can be reduced as compared with administration as an oral preparation and, moreover, since variation in the blood drug concentration is small, stable drug efficacy can be expected. In addition, since a change in the symptom due to interruption of dosing does not occur, the therapeutic effect is expected to be clearer.

The remedy or preventive for hormone-independent cancer, the hormone-independent cancer cell proliferation inhibitor, the cancer cell apoptosis inducer, the remedy or preventive for not only cancer accompanying vascularization and requiring this, but also cancer not requiring vascularization, and the remedy or preventive for recurred cancer of the present invention (hereinafter, abbreviated as the present agent in some cases) may be used for therapy in combination with hormone therapy by hormone drugs.

That is, the present invention include a remedy or a preventive for hormone-independent cancer, and a remedy or a preventive for recurred cancer, which comprises a combination of the compound having an angiotensin II antagonism, its prodrug or a salt thereof, and a hormone drug.

When the compound having an angiotensin II antagonism, its prodrug or a salt thereof is used in combination with a hormone drug, respective drugs may be formulated by mixing them with a pharmaceutically acceptable carrier separately or simultaneously, and they can be administered orally or parenterally as pharmaceutical composition(s). When drugs are formulated into preparations separately, the separately formulated preparations may be administered by mixing them using a diluent upon use, or the separately formulated individual preparations may be administered to the same subject simultaneously or separately with a certain time lag.

The hormone drug is not particularly limited as far as it is a pharmacologically useful hormone drug. For example, a hormone drug having a molecular weight of about 300 to about 40,000, preferably about 400 to about 30,000, further preferably about 500 to about 20,000 is preferable.

Specific examples include luteinizing hormone-releasing hormone (LH-RH), estrogen preparation, estrogen antagonistic preparation (tamoxifen etc.), androgen preparation, androgen antagonistic preparation (flutamide, bicalutamide, cyproterone acetate), aromatase inhibiting drug, 5α-reductase inhibitor, lyase inhibitor, insulin, somatostatin, growth hormone, growth hormone-releasing hormone (GH-RH), androgen reducing agent, estrogen reducing agent, prolactin, erythropoietin, adrenal cortical hormone, melanocyte-stimulating hormone, thyroid hormone-releasing hormone, thyroid-stimulating hormone, luteinizing hormone, luteohormone, ovarian follicle-stimulating hormone, vasopressin, oxytocin, calcitonin, gastrin, secretin, pancreozymin, cholecystokinin, angiotensin, human placenta lactogen, human chorionic gonadotropin, enkephalin, endorphin, kyotorphin, tuftsin, thymopoietin, thymosin, thymostimulin, thymus humor factor, blood thymus factor, tumor necrosis factor, colony inducing factor, motilin, dynorphin, bombesin, neurotensin, cerulein, bradykinin, atrial sodium secretion increasing factor, nerve growth factor, nerve nutrition factor, peptides having endothelin antagonism, and derivatives thereof (e.g. agonist, antagonist etc.) and fragments thereof, and derivatives of fragments.

The hormone drug may be a pharmacologically acceptable salt. When the hormone drug has a basic group such as an amino group, examples of such a salt include salts with inorganic acids (e.g. hydrochloric acid, sulfuric acid, nitric acid, boric acid etc.), and organic acids (e.g. carbonic acid, bicarbonic acid, succinic acid, acetic acid, propionic acid, trifluoroacetic acid etc.).

When the hormone drug has an acidic group such as a carboxyl group, example of the salt include salts with inorganic bases (e.g. alkali metals such as sodium, potassium etc., and alkaline earth metals such as calcium, magnesium etc.) or organic bases (e.g. organic amines such as triethylamine, basic amino acids such as arginine etc.). Alternatively, the hormone drug may form a metal complex compound (e.g. copper complex, zinc complex etc.).

As a preferable example of the aforementioned hormone drug, drugs effective for cancer in which a receptor is expressed are preferable. Specifically, LH-RH derivatives (e.g. LH-RH agonist or antagonist) and androgen antagonistic preparations (bicalutamide etc.) which are effective for sex hormone-dependent cancer such as prostate cancer, ovary cancer, uterus cervical cancer and breast cancer (in particular, prostate cancer and breast cancer) are preferable.

Specific examples of the LH-RH derivative include peptides described in Treatment with GnRH analogs: Controversies and perspectives, published by The Parthenon Publishing Group Ltd. in 1996, Japanese Patent No. 936349, JP-A 3-503165, JP-A 3-101695, JP-A 7-97334 and JP-A 8-259460.

The LH-RH derivative may be a pharmacologically acceptable salt, and examples of such a salt include pharmacologically acceptable salts of the aforementioned hormone drug.

Examples of the LH-RH derivative include a LH-RH agonist and a LH-RH antagonist, and as the LH-RH antagonist, for example, a peptide represented by the general formula [I]:

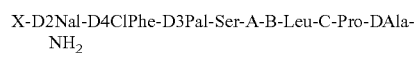

wherein X denotes $N(4H_2$-furoyl)Gly or NAc, A denotes a residue selected from NMeTyr, Tyr, Aph(Atz) and NMeAph (Atz), B denotes a residue selected from Dlys(Nic), DCit, Dlys(AzaglyNic), DLys(AzaglyFur), DhArg($Et_2$), DAph (Atz) and DhCi, C denotes Lys(Nisp), Arg or hArg($Et_2$), or a salt thereof can be used.

As the LH-RH agonist, for example, a peptide represented by the formula [II]:

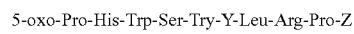

wherein Y denotes a residue selected from DLeu, DAla, DTrp, DSer(tBu), D2Nal and DHis(ImBzl), and Z denotes $NH$—$C_2H_5$ or Gly-$NH_2$, or a salt thereof is used. In particular, the peptide wherein Y is DLeu and Z is $NH$—$C_2H_5$ (leuprorelin) or a salt thereof (e.g. acetate etc.) (5-oxo-Pro-His-Trp-Ser-Tyr-DLeu-Leu-Arg-Pro-LH-$C_2H_5$ or acetate thereof) is preferable.

These peptides can be prepared by the methods described in the aforementioned publications or gazettes or similar methods.

Preferable examples of the LH-RH agonist include, in addition to the aforementioned leuprorelin (leuprorelin acetate):
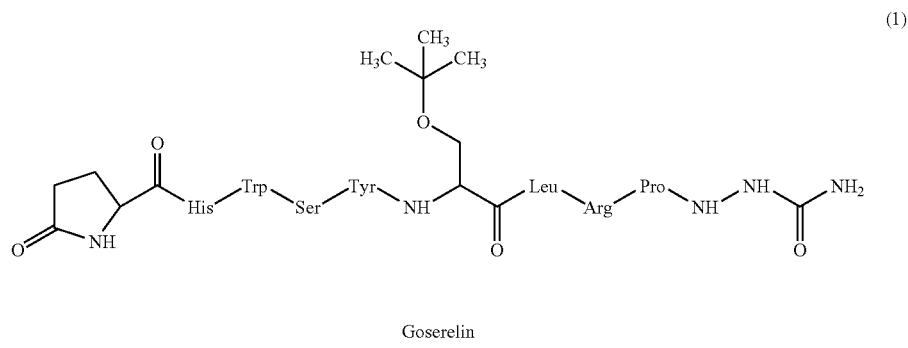
(1)
Goserelin
(U.S. Pat. No. 4,100,274, JP-A No. 52-136172),
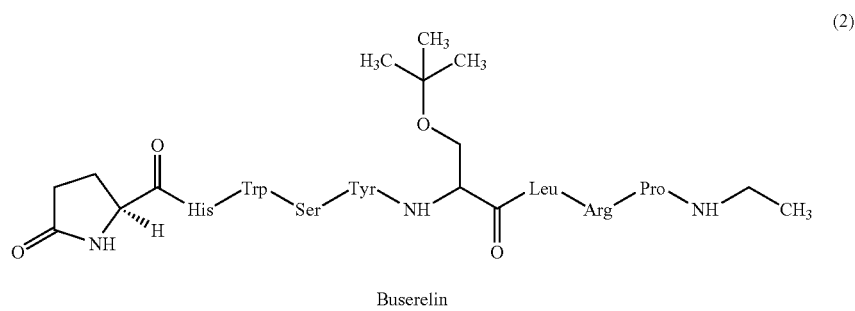
(2)
Buserelin
(U.S. Pat. No. 4,024,248, German Patent No. 2438352, JP-A No. 51-41359),
(U.S. Pat. No. 4,010,125, JP-A No. 52-31073),
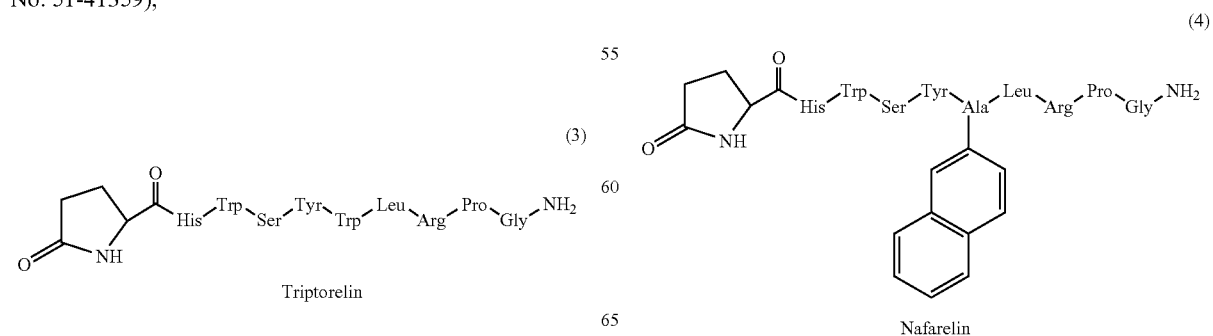
(3) Triptorelin
(4) Nafarelin (U.S. Pat. No. 4,234,571, JP-A 55-164663, JP-A 63-264498, JP-A 64-25794),

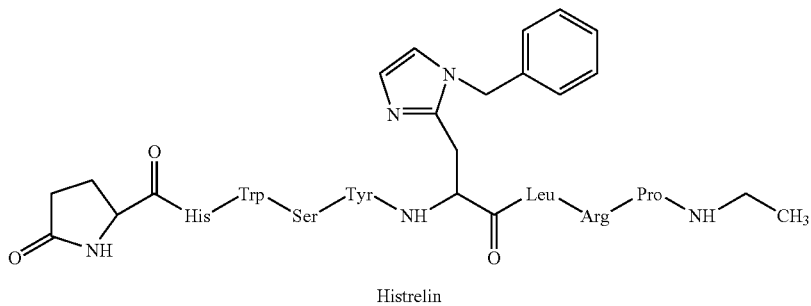
Histrelin

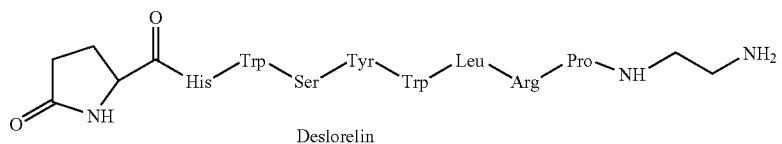
Deslorelin (U.S. Pat. No. 4,569,967, U.S. Pat. No. 4,218,439),

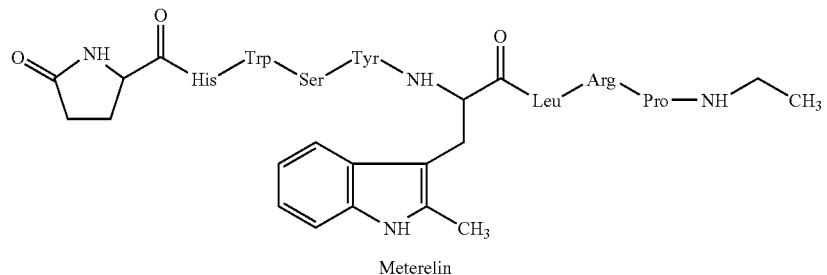
Meterelin (PCT WO 91/18016),

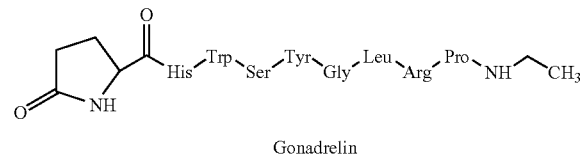
Gonadrelin (German Patent No. 2213734), and salts thereof.

Further, as the hormone drug, estrogen preparation (fosfestrol etc.), estrogen antagonistic preparation (tamoxifen etc.), androgen preparation, androgen antagonistic preparation (flutamide, bicalutamide, cyproterone acetate etc.), aromatase inhibitor, 5α-reductase inhibitor, androgen reducing agent, estrogen reducing agent, and luteohormone are preferable.

Further, the present agent may be used together a drug which inhibits the action of a cell growth factor or a receptor thereof. That is, the present invention includes:

(1) a remedy or a preventive for hormone-independent cancer, which comprises a combination of (i) the compound having an angiotensin II antagonism, its prodrug or a salt thereof and (ii) a drug which inhibits the action of a cell growth factor or a receptor thereof, and further, a remedy or a preventive for not only cancer accompanying vascularization and requiring this, but also cancer not requiring vascularization, and a remedy or a preventive for recurred or recrudescent cancer;

(2) a remedy or a preventive for hormone-independent cancer, which comprises a combination of (i) the compound having an angiotensin II antagonism, its prodrug or a salt thereof, (ii) a hormone drug and (iii) a drug which inhibits the action of a cell growth factor or a receptor thereof, and further, a remedy or a preventive for not only cancer accompanying vascularization and requiring this, but also cancer not requiring vascularization, and a remedy or a preventive for recurred cancer; and the like.

As a cell growth factor, any substances which promote cell growth may be used. The factor is usually a low-molecular peptide having a molecular weight of 20,000 or smaller and, by binding with a receptor, the action is exerted at a low concentration.

Examples of the growth factor include:
(i) EGF (epidermal growth factor) or a substance having the substantially same activity as that of EGF (e.g. EGF, heregulin (HER2 ligand) etc.),
(ii) insulin or a substance having the substantially same activity as that of insulin (e.g. insulin, IGF (insulin-like growth factor)-1, IGF-2 etc.),
(iii) FGF (fibroblast growth factor) or a substance having the substantially same activity as that of FGF (e.g. aFGF, bFGF, KGF (Keratindcyte Growth Factor), HGF (Hepatocyte Growth Factor), FGF-10 etc.),
(iv) other cell growth factors (e.g. CSF (colony stimulating factor), EPO (erythropoietin), IL-2 (interleukin-2), IL-6 (interleukin-6), NGF (nerve growth factor), PDGF (platlet-derived growth factor), TGFβ (transforming growth factor β).

The drug which inhibits the action of a cell growth factor or a receptor thereof may be a pharmacologically acceptable salt. When the drug which inhibits the action of a cell growth factor or a receptor thereof has a basic group such as an amino group, examples of such a salt include salts with inorganic salts (e.g. hydrochloric acid, sulfuric acid, nitric acid, boric acid etc.), or organic acids (e.g. carbonic acid, bicarbonic acid, succinic acid, acetic acid, propionic acid, trifluoroacetic acid etc.).

When the drug which inhibits the action of a cell growth factor or a receptor thereof has an acidic group such as a carboxyl group, example of the salt include salts with inorganic bases (e.g. alkali metals such as sodium, potassium etc.), and alkaline earth metals such as calcium, magnesium etc.) or organic bases (e.g. organic amines such as triethylamine, and basic amino acids such as arginine). Alternatively, the drug which inhibits the action of a cell growth factor or a receptor thereof may form a metal complex compound (e.g. copper complex, zinc complex etc.).

As the receptor of a cell growth factor, any receptors capable of binding to the aforementioned cell growth factor may be used. Examples thereof include EGF receptor, heregulin receptor (HER2), insulin receptor-1, insulin receptor-2, IGF receptor, FGF receptor-1 and FGF receptor-2.

Examples of the drug which inhibits the action of a cell growth factor or a receptor thereof include Herbimycin, and PD153035 (Science 265 (5175) p1093, (1994)).

In addition, examples of the drug which inhibits the action of a cell growth factor or a receptor thereof include HER2 inhibitor, and tyrosine kinase inhibitor such as Glivec (imatinib mesylate) and Iressa (gefitinib, ZD1839). As the HER2 inhibitor, any of an antibody (e.g. Herceptin), a low-molecular compound (synthetic compound, natural substance), an antisense, a HER2 ligand, heregulin and substances in which a part of these structures is modified or altered may be used as far as they are a substance which inhibits the activity (e.g. phosphorylation activity) of HER2. Alternatively, substances which indirectly inhibit the HER2 activity by inhibiting a HER2 receptor, such as a HER2 receptor antibody, may be used.

Examples of the low-molecular compound having the HER2 inhibiting activity include compounds described in WO98/03505, specifically, 1-[3-[4-[2-[(E)-2-phenylethe-nyl]-4-oxazolylmethoxy]phenyl]propyl]-1,2,4-triazole, and a compound described in WO 01/77107, that is, a compound represented by the formula:

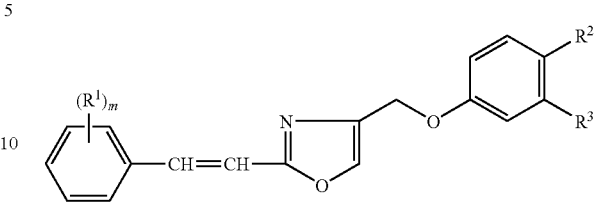

wherein m denotes 1 or 2, $R^1$ denotes a halogen atom or an optionally halogenated $C_{1-2}$alkyl group, one of $R^2$ and $R^3$ denotes a hydrogen atom, the other denotes a group represented by the formula:

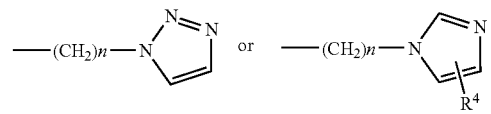

wherein n denotes 3 or 4, and $R^4$ denotes a $C_{1-4}$alkyl group substituted with 1 to 2 hydroxy group(s), or a salt thereof, preferably, 1-(4-{4-[(2-{(E)-2-[4-(trifluoromethyl)phenyl]ethenyl}-1,3-oxazol-4-yl)methoxy]phenyl}butyl)-1H-1,2,3-triazole, 1-(3-{3-[(2-{(E)-2-[4-(trifluoromethyl)phenyl]ethenyl}-1,3-oxazol-4-yl)methoxy]phenyl}propyl)-1H-1,2,3-triazole, 3-(1-{4-[4-({2-[(E)-2-(2,4-difluorophenyl)ethenyl]-1,3-oxazol-4-yl}methoxy)phenyl]butyl}-1H-imidazol-2-yl)-1,2-propanediol, or a salt thereof.

When the hormone drug and/or the drug which inhibits action of a cell growth factor or a receptor thereof are used in combination with each other, respective drugs are mixed with a pharmacologically acceptable carrier separately or simultaneously to formulate them into preparation(s), and the mixture can be orally or parenterally administered as pharmaceutical composition(s). When drugs are separately formulated into preparations, the separately formulated preparations are mixed using a diluent upon use, and can be administered. Alternatively, the separately formulated individual preparations may be administered to the same subject simultaneously or separately with a certain time lag. A kit product for mixing separately formulated preparations using a diluent upon use, and administering the mixture (e.g. an injectable kit comprising ampoules containing powdery individual drugs, and a diluent for dissolving two or more drugs by mixing upon use), and a kit product for administering separately formulated individual preparations to the same subject simultaneously or separately with a certain time lag (e.g. a tablet kit for administering two or more kinds of tablets simultaneously or separately with a certain time lag, in which tablets containing individual drugs are placed into the same or different bags and, if necessary, a column for describing drug administering times is provided) are included in the present invention.

When the hormone drug and/or the drug which inhibits action of a cell growth factor or, a receptor thereof are used in combination with each other, the dosage, administration time, administration frequency, and administration intervals of respective drugs are preferably used in a generally acceptable range.

For example, it is preferable that the drug which inhibits action of a cell growth factor or a receptor thereof in the present invention is administered after administration of the hormone drug, for example, at the moment when the effective blood concentration of the hormone drug is reduced below about 50%, or at the moment when a receptor of a cell growth factor is initiated to be expressed by administration of the hormone drug. If necessary, administration may be initiated earlier.

The hormone drug and/or the drug which inhibits action of a cell growth factor or a receptor thereof can be formulated into solid preparations such as tablets, capsules (including soft capsules and microcapsules), granules, powders, and suppositories; or liquid preparations such as syrups and injectable preparations, or sustained-release preparations, by incorporating a pharmacologically acceptable carrier into the hormone drug and, if necessary, the drug which inhibits action of a cell growth factor or a receptor thereof, and those preparations can be administered orally or parenterally. Alternatively, the hormone drug and the drug which inhibits action of a cell growth factor or a receptor thereof may be formulated into preparations separately.

As the pharmaceutically acceptable carrier, various organic or inorganic carrier substances which are conventionally used as a pharmaceutical material are used, and they are incorporated as an excipient, a lubricant, a binder or a disintegrating agent in solid preparations; or as a solvent, a solubilizer, a suspending agent, an isotonic, a buffer, or a soothing agent in liquid preparations. If necessary, additives such as an antiseptic, an antioxidant, a coloring agent, and a sweetener may be used.

Preferable examples of the excipient include lactose, white sugar, D-mannitol, starch, crystalline cellulose, and light silicic acid anhydride.

Preferable examples of the lubricant include magnesium stearate, calcium stearate, talc, colloidal silica.

Preferable examples of the binder include crystalline cellulose, white sugar, D-mannitol, dextrin, hydroxypropylcellulose, hydroxypropylmethylcellulose, and polyvinylpyrrolidone.

Preferable examples of the disintegrating agent include starch, carboxymethylcellulose, calcium carboxymethylcellulose, sodium crosscarmerose, and sodium carboxymethylstarch.

Preferable examples of the solvent include water for injection, alcohol, propylene glycol, macrogol, sesame oil, corn oil.

Preferable examples of the solubilizer include polyethylene glycol, propylene glycol, D-mannitol, benzyl benzoate, ethanol, trisaminomethane, cholesterol, triethanolamine, sodium carbonate, and sodium citrate.

Preferable examples of the suspending agent include surfactants such as stearyltriethanolamine, sodium laurylsulfate, laurylaminopropionic acid, lecithin, benzalkonium chloride, benzethonium chloride, and monostearic acid glycerin; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose.

Preferable examples of the isotonic include sodium chloride, glycerin, and D-mannitol.

Preferable examples of the buffer include buffers of phosphate, acetate, carbonate, and citrate.

Preferable examples of the soothing agent include benzyl alcohol.

Preferable examples of the antiseptic include paraoxybenzoic acid esters, chlorobutanol, benzyl alcohol, phenethyl alcohol, dehydroacetic acid, and sorbic acid.

Preferable examples of the antioxidant include sulfite, and ascorbic acid.

A content of the hormone drug (active ingredient) in the preparation containing the hormone drug varies depending on the dosage form, the administration method, the carrier, etc., and is usually about 0.1 to 30% (w/w), preferably about 1 to 20% (w/w), more preferably about 5 to 10% (w/w) relative to the total amount of the preparation.

A content of the drug (active ingredient) which inhibits action of a cell growth factor or a receptor thereof in the preparation containing the drug which inhibits action a cell growth factor or a receptor thereof (particularly, in case of a low-molecular compound) varies depending on the dosage form, the administration method, the carrier, etc., and is usually about 0.1 to 90% (w/w) relative to the total amount of the preparation.

A content of various additives is usually about 0.1 to 99.9% (w/w), preferably about 10 to 99.9% (w/w), more preferably about 20 to 90% (w/w) relative to the total amount of the preparation.

The dosage of the hormone drug and/or the drug which inhibits action of a cell growth factor or a receptor thereof varies depending on the kind of a compound having an AII antagonism, the kind of the hormone drug, the kind of the drug which inhibits action of a cell growth factor or a receptor thereof, the administration route, the symptom, etc. For example, in case that a LH-RH derivative as an anticancer agent is subcutaneously administered to a patient (weight 40 to 80 kg) with breast cancer or prostate cancer, and that the drug which inhibits action of a cell growth factor or a receptor thereof is a low-molecular compound, the dosage in terms of the compound is preferably about 1.0 to 100 mg/kg weight, more preferably about 5.0 to 50 mg/kg weight per day. This dosage can be administered once, or by dividing into two or three times per day. Further, regarding a LH-RH derivative, the preferred dosage per day in terms of the compound is about 1.0 to 100 mg/kg weight, more preferably about 1.0 to 50 mg/kg weight, for example, in case of a patient (weight 40 to 80 kg) with breast cancer or prostate cancer. Furthermore, when the drug which inhibits action of a cell growth factor or a receptor thereof is an antibody, usually, it can be administered intravenously, subcutaneously, or tumor-topically at a dosage of about 1 to 2,000 mg/kg/week, preferably about 5 to 1,000 mg/kg/week for successive days or intermittently.

A LH-RH agonist or antagonist which is preferably used as the hormone drug (preferably, a peptide represented by the formula: 5-oxo-Pro-His-Trp-Ser-Tyr-DLeu-Leu-Arg-Pro-NH—$C_2H_5$ or a salt thereof), more preferably leuprorelin acetate is administered preferably as a sustained-release injectable preparation. When a sustained-release preparation is sustained-release type microcapsules, long term sustained-release type microcapsules which release the LH-RH agonist or antagonist over 2 months or longer is preferable. A sustained-release preparation (particularly, sustained-release type microcapsules) containing such a LH-RH agonist or antagonist can be prepared by a known per se methods, for example, the methods described in JP-A 60-100516, JP-A 62-201816, JP-A 4-321622, JP-A 6-192068, JP-A 9-132524, JP-A 9-221417, JP-A 11-279054, and WO 99/360099.

Among the aforementioned sustained-release preparations, in particular, the "long term sustained-release type microcapsules which release a physiologically active substance at a zero order over 2 months or longer" described in JP-A 4-321622 is preferably used.

When a sustained-release preparation (an agent containing sustained-release type microcapsules) containing a LH-RH agonist or antagonist (preferably leuprorelin or a salt thereof, more preferably leuprorelin acetate) is administered as an injectable preparation, the dosage is varies depending on the drug sustained-release term of the sustained-release type microcapsules. For example, when the preparation is administered once in about 1 month, for example, in an adult patient (weight 60 kg) with prostate cancer, usually, the LH-RH agonist or antagonist (preferably leuprorelin or a salt thereof, more preferably leuprorelin acetate) may be administered subcutaneously or intramuscularlly at a dosage of about 0.01 to 20 mg, preferably about 0.1 to 10 mg, more preferably about 0.1 to 5 mg per each dosing. For example, when the preparation is administered once in about 3 months, for example, in an adult patient (weight 60 kg) with prostate cancer, usually, the LH-RH agonist or antagonist (preferably leuprorelin or a salt thereof, more preferably leuprorelin acetate) is may be administered subcutaneously or intramuscularly at a dosage of about 0.1 to 30 mg, preferably about 0.1 to 20 mg more preferably about 1 to 15 mg per each dosing.

In case of other animals, a dosage in terms of 60 kg can be administered.

Alternatively, when the LH-RH agonist or antagonist is used as the hormone drug, it may be administered with an anti-estrogen agent (e.g. tamoxifen etc.) for preventing or treating prostate cancer or breast cancer.

Hormone therapy using the hormone drug such as a LH-RH agonist and an anti-androgen agent is applied to a patient with hormone-dependent cancer (prostate cancer etc.) by the aforementioned usage. However, when administration is continued for a long term, a cancer tissue or a metastasized lesion is converted into hormone-independent in some cases by proliferation of hormone-independent cancer cells or hormone-independent metastasized cancer cells.

At such a transition stage, cancer can be effectively treated by continuously using the hormone drug according to the aforementioned conventional usage, in combination with the use of the remedy or the preventive for hormone-independent cancer containing the compound having an AII antagonism of the present invention, its prodrug or a salt thereof at a time when a tendency of transition to independency appears.

[1] For example, in case of treatment of prostate cancer, an optimal combination of drugs, dosages, and administration time are selected according to the symptom, the stage, and the age of a cancer patient, for example, by using a prostate-specific antigen (PSA) and a differentiation degree of cancer cells as indexes.

The blood PSA concentration can be measured using a clinical PSA measuring kit (Markit MPA etc.).

According to the rule used by Society of Japan Urology, a stage of prostate cancer is roughly classified into four groups, i.e., 1. the case where cancer is limited in prostate, 2. the case where cancer is extended to a periphery of prostate, but is not metastasized, 3. the case where lymph node metastasis is observed and 4. the case where remote metastasis is observed (National Cancer Center HP).

Stage A: Cancer accidentally found in an excised tissue by operation under diagnosis of not cancer but benign lesion (accidental cancer).

A1: Highly differentiated cancer of a 1.0 cm or smaller lesion which is limited in prostate.

A2: Cancer which is extended in prostate diffusely (the state where cancer is not limited to one place but is extended), or moderately or slightly differentiated cancer (highly malignant cancer as compared with high differentiation).

The following stage is a stage which is histologically diagnosed to be cancer by aspirated cell examination or needle biopsy after clinical suspicion of prostate cancer.

Stage B: Cancer which is limited in prostate.

B1: 1.5 cm or smaller cancer in which a lesion is limited to either one of a left part and a right part of prostate.

B2: Cancer larger than 1.5 cm in prostate, or cancer which is extended diffusely or tuberously (the state where cancer is grown as a mass).

Stage C: Cancer which is extended over a prostate capsule, but in which metastasis is not observed, including cancer which is extended to seminal vesicle adjacent to prostate, and a cervical part of bladder.

Stage D: Cancer in which a clinically clear metastasized lesion is observed (a size of cancer in prostate is not prescribed).

D1: Cancer in which lymph node metastasis in pelvic is observed as prescribed in the rule.

D2: Cancer in which metastasis in a broader range than that of D1 to a remote part such as lymph node, lung and liver is observed.

Hormone therapy is desirably performed on a patient at a stage B or higher. It is preferable that a one month sustained-release preparation of leuprin is administered to these patients once every 4 weeks, a 3 months preparation is administered once every 12 weeks, a 4 months preparation is administered once every 16 weeks, and a 6 months preparation is administered once every 24 weeks by injection. Preferably, these are used in combination with an anti-androgen agent according to appropriate usage at a suitable dosage.

It is preferable that the compound having an AII antagonism (preferably Candesartan cilexetil, Candesartan) is administered to a patient who has become hormone-independent (a patient at the Stage D or higher) after such a hormone therapy was continued, according to appropriate usage at a suitable dosage at a time when increase in a PSA value is recognized or, if necessary, earlier.

It is preferable that, even when PSA is confirmed to be reduced below a detection limit of a measuring kit by the aforementioned therapy, administration of the remedy or the preventive for hormone-independent cancer containing the compound having an AII antagonism of the present invention, its prodrug or a salt thereof and/or hormone therapy is (are) continued, though they may be intermitted or stopped.

However, when so-called recurrence is confirmed, such as the case where a PSA value reduced by the therapy increases again, the case where metastasis or a new lesion is observed in lymph node or other organ (i.e. a patient of the stage D), or the case where tumor is observed at a primary site or other site after surgical treatment (e.g. radical prostectomy), the present agent may be applied as described above.

[2] For example, in case of treatment of breast cancer, an optimal combination of drugs, dosages, and administration time are selected according to the symptom, the stage, and the age of a cancer patient, for example, by using an expression amount of estrogen receptor, progesterone receptor, EGF receptor or HER2, and a degree of differentiation of cancer cells as indexes.

For a patient before menopause, it is preferable to administrate once for 4 weeks in case of 1 month sustained-release preparations of leuprin, once every 16 weeks in case of 4 months sustained-release preparations, and once every 24 weeks in case of 6 months sustained-release preparations by injection. These are used in combination with an anti-estrogen agent according to appropriate usage at a suitable dosage.

It is preferable that the compound having an AII antagonism (preferably a sustained-release preparation of Candesartan) is administered to a patient who has become hormone-independent after such a hormone therapy was continued, according to appropriate usage at a suitable dosage at a time when recurrence is recognized (that is, a patient at the Stage D described above) or, if necessary, earlier.

In case of a patient before menopause, preferably, these are used in combination with an anti-estrogen agent, estrogen synthesis inhibitor or the like according to appropriate usage at a suitable dosage.

It is preferable that the compound having an AII antagonism (preferably, Candesartan cilexetile, Candesartan) is administered to a patient who has become hormone-independent after such a hormone therapy was continued, according to appropriate usage at a suitable dosage at a time when recurrence is recognized (that is, a patient at the Stage D described above) or, if necessary, earlier.

It is preferable that, even when the disappearance of tumor by the above-mentioned therapy is confirmed, administration of the remedy or the preventive for hormone-independent cancer containing the compound having an AII antagonism of the present invention, its prodrug or a salt thereof and/or hormone therapy is (are) continued, though they may be intermitted or stopped.

However, when so-called recurrence is confirmed, such as the case where metastasis or a new lesion is observed in lymph node or other organ (i.e. a patient of the Stage D described above), or the case where tumor is observed at a primary site or other site after surgical treatment, the present agent may be applied as described above.

Further, depending on the symptom, systemic conditions, stage and age of a cancer patient, and nature of cancer cells (differentiation degree), other active ingredients, for example, a chemical therapeutic or an immunological therapeutic may be incorporated into the present agent, or may be used in combination with the present agent. Furthermore, radiation therapy or surgical treatment for cancer may be combined.

As the chemotherapeutic, for example, alkylating agents (e.g. cyclophosphamide, ifosfamide, estramustine sodium phosphate), metabolism antagonists (e.g. methotrexate, 5-fluorouracil), anti-cancer antibiotics (e.g. mitomycin, adriamycin), plant-derived anticancer agents (e.g. vincristine, vindesine, toxal), cisplatin, carboplatin, and etopoxide are used.

As the immunological therapeutic, for example, microorganisms or microbial cell components (e.g. muramyldipeptide derivative, picibanil), polysaccharides having immunological enhancement activity (e.g. lentinan, sizofiran, krestin), and cytokines (e.g. interferon, interleukin) are used.

Alternatively, the present agent may be used together with other drug ingredients including a vasodilator, a hyperlipemia treating drug, a hypertension treating drug, a chronic heart failure treating drug, a nephrosis syndrome treating drug, a chronic renal failure treating drug, a gastric or duodenal ulcer treating drug, a baliary disease treating drug, an anti-tumor agent, a infectious treating drug, a thrombus formation treating drug and an anti-inflammatory. In this case, these compounds may be administered as an oral preparation or, if necessary, may be administered in the form of a suppository as a rectal preparation. Examples of the ingredient which can be combined include β receptor blockers [e.g. propranolol, nipradilol, atenolol, carvedilol etc.], α receptor regulators [e.g. prazosin, clonidine etc.], nitrous acid drug [e.g. nitroglycerin, isosorbide dinitrate etc.] diuretic [e.g. spironolactone, furosemide, chlorothiazide etc.], and endothelin antagonist.

Alternatively, the following combination with various therapeutics is also possible.

Vasodilator: nifedipine, diltiazem, nicorandil, nitrous acid agent etc.;

Hypertension treating drug: ACE inhibitor [e.g. enalapril maleate etc.], Ca antagonist [e.g. manidipine, amlodipine etc.], etc.;

Hyperlipemia; HMG-CoA reductase inhibitor [e.g. atrovastatin, cerivastatin etc.], fibrate drug [e.g. clofibrate, bezafibrate etc.], squalene synthesis enzyme inhibitor, etc.;

Chronic heart failure treating drug: cardiotonic drug [e.g. cardiac glycoside (digoxin etc.), PDE inhibitor etc.], ACE inhibitor [e.g. enalapril maleate etc.], Ca antagonism [e.g. amlodipine etc.], β receptor blocker, etc.;

Chronic renal treating drug: depressor [e.g. ACE inhibitor (enalapril maleate etc.) and Ca antagonist (manidipine etc.), α receptor blocker etc.], etc.;

Gastric-duodenal ulcer treating drug: antacid [e.g. hystamine H2 antagonist (cimepidine etc.), proton pump inhibitor (lansoprazole etc.) etc.], etc.;

Biliary disease treating drug: choleretic [e.g. dehydrocholic acid etc.], cholekinetic [e.g. magnesium sulfate etc.], etc.;

Anti-tumor drug: alkylating agent, metabolism antagonist, anti-tumorigenic antibiotic preparation, anti-tumorigenic plant component preparation and other anti-tumor drug;

Infectious disease treating drug: [e.g. antibiotic preparation (cefotiam dihydrochloride, cefozopran hydrochloride, ampicillin etc.), chemotheraputic (sulfa agent, synthetic antibacterium agent, anti-virus agent etc.), biological preparation (vaccines, blood preparations such as immunoglobulin) etc.], etc.;

Thrombus formation treating drug: blood coagulation inhibitor [e.g. heparin sodium, heparin potassium, warfarin potassium, blood coagulation factor Xa inhibitor as well as a drug having the function of correcting balance of fibrinolysis system], thrombolytic blood [e.g. tPA, urokinase], anti-platelet drug [e.g. aspirin, sulphinpyrazolo, dipyritamole, ticlopidine (panaldine), cilostazol, GPIIb/IIIa antagonist etc.], etc.;

Anti-inflammatory: aspirin, acetaminophen, non-steroidal anti-inflammatory [e.g. indometacin etc.], steroid agent [e.g. dexamethasone etc.], etc.

The present agent can be used together with these various drugs simultaneously or with a certain time lag.

When these drugs are used in combination of the present agent, each drug may be formulated into a preparation separately or simultaneously by mixing with a pharmacologically acceptable carrier, an excipient, a binder, a diluent, etc., and may be orally or parenterally administered as a pharmaceutical composition. When drugs are formulated into preparations separately, the separately formulated preparations can be administered by mixing using a diluent upon use. Separately formulated individual preparations may be administered to the same subject simultaneously or separately with a certain time lag. A kit product for mixing separately formulated preparations, using a diluent upon use, and administering the mixture (e.g. an injectable kit containing ampoules containing powdery individual drugs, and a diluent for dissolving two or more drugs by mixing upon use), and a kit product for administering separately formulated individual preparations to the same subject simultaneously or separately with a certain time lag (e.g. a tablet kit for administering two or more kinds of tablets simultaneously or separately with a certain time lag, in which tablets containing individual drugs are placed into the same or different bags and, if necessary, a column for describing drug administering times is provided) are included in the medicament of the present invention.

The meanings of abbreviations used herein are as follows:

| Abbreviations: | Name |
| --- | --- |
| 5-oxo-Pro: | Pyroglutamic acid residue |
| His: | Histidine residue |
| Trp: | Tryptophan residue |
| Ser: | Serine residue |
| Tyr: | Tyrosine residue |
| Leu: | Leucine residue |
| Arg: | Arginine residue |
| Pro: | Proline residue |
| DLeu: | D-leucine residue |
| DAla: | D-alanine residue |
| DTrp: | D-tryptophan residue |
| N(4H$_2$-furoyl)Gly: | N-tetrahydrofuroylglycine residue |
| NAc: | N-acetyl group |
| D2Nal: | D-3-(2-naphtyl)alanine residue |
| D4ClPhe: | D-3-(4-chloro)phenylalanine residue |
| D3Pal: | D-3-(3-pyridyl)alanine residue |
| NMeTyr: | N-methyltyrosine residue |
| Aph(Atz): | N-[5'-(3'-amino-1'H-1',2',4'-triazolyl)]phenylalanine residue |
| NMeAph(Atz): | N-methyl-[5'-(3'-amino-1'H-1',2',4'-triazolyl)]phenylalanine residue |
| DLys(Nic): | D-(e-N-nicotinoyl)lysine residue |
| Dcit: | D-citrulline residue |
| DLys(AzaglyNic): | D-(azaglicylnicotinoyl)lysine residue |
| DLys(AzaglyFur): | D-(azaglicylfuranyl)lysine residue |
| DhArg(Et$_2$): | D-(N,N'-diethyl)homoarginine residue |
| DAph(Atz): | D-N-[5'-(3'-amino-1'H-1',2',4'-triazolyl)]phenylalanine residue |
| DhCi: | D-homocitrulline residue |
| Lys(Nisp): | (e-N-isopropyl)lysine residue |
| hArg(Et2): | (N,N'-diethyl)homoarginine residue |
| DSer(tBu): | D-O-(t-butyl)serine residue |
| DHis(ImBzl): | N$^r$-butylhistidine residue |

Designation of amino acids by abbreviations is based on abbreviations by IUPAC-IUB Commission on Biochemical Nomenclature, European Journal of Biochemistry, vol. 138, p9-37 (1984) or conventional abbreviations in the art. In addition, when there is a possibility that an amino acids has an optical isomer, designation indicates a L-amino acid unless otherwise indicated.

The following Reference Examples and Examples will further illustrate the present invention in detail but the present invention is not limited by them.

EXAMPLES

The anticancer agents such as the remedy or the preventive for hormone-independent cancer, the hormone-independent cancer cell proliferation inhibitor, and the cancer cell apoptosis inducer comprising the compound having an AII antagonism a salt thereof as an active ingredient of the present invention or can be prepared, for example, by the following formulations.

Reference Example 1

In a mixed solution of 3.5 ml of dichloromethane and 1.5 ml of methanol, 0.25 g of 2-ethoxy-1-[[2'-(4,5-dihydro-5-oxo-1,2,4-oxadiazol-3-yl)biphenyl-4-yl]methyl]benzimidazole-7-carboxylic acid (hereinafter, abbreviated as Compound A), and 2.25 g of lactic acid-glycolic acid copolymer (lactic acid/glycolic acid=75/25 (mol %), weight average molecular weight 10,700, number average molecular weight 6,100, number average molecular weight by terminal group quantitation 3,700, manufactured by Wako Pure Chemical Industries, Ltd.) were dissolved. The solution was poured into 500 ml of a 0.1% (w/w) aqueous polyvinyl alcohol solution maintained at 18° C. in advance and the mixture was emulsified at 7,000 rpm with a turbine-type homomixer to prepare an O/W emulsion. This O/W emulsion was stirred at room temperature for 3 hours to volatilize dichloromethane and methanol. After solidification of an oily phase, it was collected by centrifugation at 2,000 rpm. This was dispersed into distilled water again, and the dispersion was centrifuged to wash away freed drugs. The collected microcapsules were dispersed again by addition of a small amount of distilled water, and then, the dispersion was lyophilized to obtain a powder. A recovery rate was 69%, an encapsulation rate of Compound A into the microcapsules was 92%, and a content of Compound A in the microcapsules was 9.2%.

Reference Example 2

A solution obtained by dissolving 0.25 g of a disodium salt of Compound A in 0.4 ml of distilled water was mixed with a solution obtained by dissolving 2.25 g of a lactic acid-glycolic acid copolymer (as in Reference Example 1) in 4 ml of dichloromethane, and the mixture was emulsified with a homogenizer to form a W/O emulsion. Then, this W/O emulsion was poured into 500 ml of a 0.1% (w/w) aqueous polyvinyl alcohol solution maintained at 18° C. in advance, and emulsified at 7,000 rpm with a turbine-type homomixer to prepare a W/O/W emulsion. This W/O/W emulsion was stirred at room temperature for 3 hours to volatilize dichloromethane. After solidification of an oily phase, it was collected by centrifugation at 2,000 rpm. This was dispersed into distilled water again, and the dispersion was centrifuged to wash away freed drugs. The collected microcapsules were dispersed again by addition of a small amount of distilled water, and then the dispersion was lyophilized to obtain a powder. A recovery rate was 50%, an encapsulation rate of Compound A in the microcapsules was 37%, and a content of Compound A in the microcapsules was 3.7%.

Reference Example 3

In a mixed solution of 3.5 ml of dichloromethane and 2.5 ml of methanol, 0.4 g of Compound A and 1.6 g of a lactic acid polymer ethyl ester (a biodegradable polymer obtained by ethyl-esterifying a terminal carboxyl group of a lactic acid polymer, weight average molecular weight 10,200, number average molecular weight 5,680, manufactured by Wako Pure Chemical Industries, Ltd.) were dissolved, and the mixture was poured into 800 ml of a 0.1% (w/w) aqueous polyvinyl alcohol solution containing 5% mannitol which was maintained at 18° C. in advance, and the mixture was emulsified at 7,000 rpm with a turbine-type homomixer to prepare an O/W emulsion. This O/W emulsion was stirred at room temperature for 3 hours to volatilize dichloromethane and methanol. After solidification of an oily phase, it was collected by centrifugation at 2,000 rpm. This was dispersed into distilled water again, and the dispersion was centrifuged to wash away freed drugs. The collected microcapsules were dispersed again by addition of a small amount of distilled water, and then, the dispersion was lyophilized to obtain a powder. A recovery rate was 83%, an encapsulation rate of Compound A in the microcapsules was 86%, and a content of Compound A in the microcapsules was 17.1%.

Reference Example 4

To a solution obtained by dissolving 2.4 g of a lactic acid-glycolic acid copolymer (lactic acid/glycolic acid 75/25 (mol %), weight average molecular weight 14,000, number average molecular weight 4,200, number average molecular weight by terminal group quantitation 4,090, manufactured by Wako Pure Chemical Industries, Ltd.) in 4.5 ml of dichloromethane and 1 ml of ethanol were added 0.6 g of 2-ethoxy-1-[[2'-(1H-tetrazol-5-yl)biphenyl-4-yl]methyl]benzimidazole-7-carboxylic acid (hereinafter, abbreviated as Compound B) and 0.09 g of zinc oxide having a particle diameter of 0.02 µm. The mixture was shaken while stirring at room temperature for 12 hours to obtain a slightly clouded solution. This solution was poured into 400 ml of a 0.1% by weight aqueous polyvinyl alcohol solution maintained at 15° C. in advance, and the mixture was emulsified at 7,000 rpm with a turbine-type homomixer to prepare an O/W emulsion. This O/W emulsion was stirred at room temperature for 3 hours to volatilize dichloromethane and ethanol. After solidification of an oily phase, it was collected by centrifugation at 2,000 rpm. This was dispersed into distilled water again, followed by further centrifugation to wash away freed drugs. The collected microcapsules were dispersed again by addition of a small amount of distilled water in which mannitol was dissolved, and then, the dispersion was lyophilized to obtain a powder. An encapsulation rate of Compound B in the microcapsules was 97%, and a content of Compound B in the microcapsules was 18.8%.

Reference Example 5

According to the same manner as that of Reference Example 1, microcapsules were obtained except that the amount of zinc oxide was changed to 0.057 g. An encapsulation rate of Compound B in the microcapsules was 97%, and a content of Compound B in the microcapsules was 19.0%.

Reference Example 6

According to the same manner as that of Example 1, microcapsules were obtained except that the amount of Compound B, the amount of zinc oxide, and the amount of a lactic acid-glycolic acid copolymer were changed to 0.9 g, 2.1 g and 0.12 g, respectively. An encapsulation rate of Compound B in the microcapsules was 96%, and a content of Compound B in the microcapsules was 27.8%.

Reference Example 7

According to the same manner as that of Reference Example 3, microcapsules were obtained except that the amount of zinc oxide was changed to 0.18 g. An encapsulation rate of Compound B in the microcapsules was 92%, and a content of Compound B in the microcapsules was 26.2%.

Reference Example 8

To a solution obtained by dissolving 4.2 g of a lactic acid-glycolic acid copolymer (lactic acid/glycolic acid 75/25 (mol %), weight average molecular weight 14,000, number average molecular weight 4,200, number average molecular weight by terminal group quantitation 4,090, manufactured by Wako Pure Chemical Industries, Ltd.) in 9 ml of dichloromethane and 1.5 ml of ethanol were added 1.8 g of Compound B and 0.3 g of zinc oxide having a particle diameter of 0.02 µm were added. The mixture was shaken while stirring at room temperature for 12 hours to obtain a slightly clouded solution. This solution was poured into 800 ml of a 0.1% by weight aqueous polyvinyl alcohol solution maintained at 15° C. in advance, and the mixture was emulsified at 7,000 rpm with a turbine-type homomixer to prepare an O/W emulsion. This O/W emulsion was stirred at room temperature for 3 hours to volatilize dichloromethane and ethanol. After solidification of an oily phase, it was collected by centrifugation at 2,000 rpm. This was dispersed into distilled water again, followed by further centrifugation to wash away freed drugs. The collected microcapsules were dispersed again by addition of a small amount of distilled water in which mannitol was dissolved, and then, the dispersion was lyophilized to obtain a powder. An encapsulation of Compound B in the microcapsules was 94%, and a content of Compound B in the microcapsules was 26.8%.

Reference Example 9

To a solution obtained by dissolving 0.7 g of a lactic acid-glycolic acid copolymer (lactic acid/glycolic acid 75/25 (mol %), weight average molecular weight 14,000, number average molecular weight 4,200, number average molecular weight by terminal group quantitation 4,090, manufactured by Wako Pure Chemical Industries, Ltd.) in 1.5 ml of dichloromethane and 1 ml of methanol were added 0.3 g of Compound A and 0.05 g of zinc oxide having a particle diameter of 0.02 µm. The mixture was shaken while stirring at room temperature for 12 hours to obtain a slightly clouded solution. This solution was poured into 300 ml of a 0.1% by weight aqueous polyvinyl alcohol solution maintained at 15° C. in advance, and the mixture was emulsified at 6,500 rpm with a turbine-type homomixer to prepare an O/W emulsion. This O/W emulsion was stirred at room temperature for 3 hours to volatilize dichloromethane, and methanol. After solidification of an oily phase, it was collected by centrifugation at 2,000 rpm. This was dispersed into distilled water again, followed by further centrifugation to wash away freed drugs. The collected microcapsules were dispersed again by addition of a small amount of distilled water in which mannitol was dissolved, and then, the dispersion was lyophilized to obtain a powder. An encapsulation rate of Compound A in the microcapsules was 91%, and a content of Compound A in the microcapsules was 25.9%.

Reference Example 10

To a solution obtained by 1.8 g of a lactic acid-glycolic acid copolymer (lactic acid/glycolic acid 75/25 (mol %), weight average molecular weight 14,000, number average molecular weight 4,200, number average molecular weight by terminal group quantitation 4,090, manufactured by Wako Pure Chemical Industries, Ltd.) in 5 ml of dichloromethane were added 1 g of Compound B and 0.18 g of zinc oxide having a particle diameter of 0.02 µm. The mixture was emulsified and mixed with a small homogenizer for 60 seconds to obtain a clouded dispersion. This dispersion was poured into 400 ml of a 0.1% by weight aqueous polyvinyl alcohol solution maintained at 15° C. in advance, and the mixture was emulsified at 8,000 rpm with a turbine-type homomixer to prepare an O/W emulsion. This O/W emulsion was stirred at room temperature for 3 hours to volatilize dichloromethane. After solidification of an oily phase, it was collected by centrifugation at 2,000 rpm. This was dispersed into distilled water again, followed by further centrifugation to wash away freed drugs. The collected microcapsules were dispersed again by addition of a small amount of distilled water in which mannitol was dissolved, and then, the dispersion was lyophilized to obtain a powder. An encapsulation rate of Compound B in the microcapsules was 96%, and a content of Compound B in the microcapsule was 32.0%.

Reference Example 11

According to the same manner as that of Example 7 microcapsules were obtained except that a slightly clouded solution obtained by adding 0.8 ml of ethanol to dichloromethane, and shaking while stirring them at room temperature for 12 hours was used. An encapsulation rate of Compound B in the microcapsules was 95%, and a content of Compound B in the microcapsules was 32.0%.

Reference Example 12

In a mixed solution of 4.5 ml of dichloromethane and 0.7 ml of ethanol, 0.9 g of 1-(cyclohexyloxycarbonyloxy)ethyl 2-ethoxy-1-[[2'-(1H-tetrazol-5-yl)biphenyl-4-yl]methyl]benzimidazole-7-carboxylate (hereinafter, abbreviated as Compound C) and 2.1 g of a lactic acid-glycolic acid copolymer (lactic acid/glycolic acid 75/25 (mol %), weight average molecular weight 14,000, number average molecular weight 4,200, number average molecular weight by terminal group quantitation 4,090, manufactured by Wako Pure Chemical Industries, Ltd.) were dissolved. To this solution was added 0.15 g of zinc oxide having a particle diameter of 0.02 µm, followed by shaking while stirring at room temperature for 12 hours to obtain a slightly clouded solution. This solution was poured into 400 ml of a 0.1% by weight aqueous polyvinyl alcohol solution maintained at 15° C. in advance, and the mixture was emulsified at 7,500 rpm with a turbine-type homomixer to prepare an O/W emulsion. This O/W emulsion was stirred at room temperature for 3 hours to volatilize dichloromethane and ethanol. After solidification of an oily phase, it was collected by centrifugation at 2,000 rpm. This was dispersed into distilled water again, followed by further centrifugation to wash away freed drugs. The collected microcapsules were dispersed again by addition of a small amount of distilled water in which minnitol was dissolved, and then, the dispersion was lyophilized to obtain a powder. An encapsulation of Compound C in the microcapsules was 96%, and a content of Compound C in the microcapsules was 27.4%.

Reference Example 13

According to the same manner as that of Reference Example 12, microcapsules were prepared except that zinc oxide was not added. An encapsulation rate of Compound C in the microcapsules was 98%, and a content of Compound C in the microcapsules was 30.0%.

Reference Example 14

In 5 ml of dichloromethane, 1.2 g of Compound C and 1.8 g of a lactic acid/glycholic acid copolymer (lactic acid/glycholic acid 75/25 (mol %), weight average molecular weight 14,000, number average molecular weight 4,200, number average molecular weight by terminal group quantitation 4,090, manufactured by Wako Pure Chemical Industries, Ltd.) were dissolved. To this solution was added 0.18 g of zinc oxide having a particle diameter of 0.02 µm. The mixture was shaken while stirring at room temperature for 1 hour to obtain a slightly clouded solution. This solution was poured into 400 ml of a 0.1% by weight aqueous polyvinyl alcohol solution maintained at 15° C. in advance, and the mixture was emulsified at 8,000 rpm with a turbine-type homomixer to prepare an O/W emulsion. This O/W emulsion was stirred at room temperature for 3 hours to volatilize dichloromethane. After solidification of an oily phase, it was collected by centrifugation at 2,000 rpm. This was dispersed into distilled water again, followed by further centrifugation to wash away freed drugs. The collected microcapsules were dispersed again by addition of a small amount of distilled water, in which mannitol was dissolved, and then, the dispersion was lyophilized to obtain a powder. An encapsulation rate of Compound C in the microcapsules was 95%, and a content of Compound C in the microcapsules was 35.9%.

Reference Example 15

According to the same manner as that of Example 4, microcapsules were prepared except that zinc oxide was not added. An encapsulation rate of Compound B in the microcapsules was 99%, and a content of Compound B in the microcapsules was 19.8%.

Reference Example 16

According to the same manner as that of Reference Example 9, microcapsules were prepared except that zinc oxide was not added. An encapsulation rate of Compound A in the microcapsules was 95%, and a content of Compound A in the microcapsules was 28.4%.

Reference Example 17

To a solution obtained by dissolving 3.6 g of a lactic acid-glycolic acid copolymer (lactic acid/glycolic acid 75/25 (mol %), weight average molecular weight 14,000, number average molecular weight 4,000, number average molecular weight by terminal group quantitation 4,090, manufactured by Wako Pure Chemical Industries, Ltd.) in 11 ml of dichloromethane and 0.4 ml of ethanol were added 2 g of 2-ethoxy-1-[[2'-(1H-tetrazol-5-yl)biphenyl-4-yl]methyl]benzimidazole-7-carboxylic acid (Compound B) and 0.36 g of zinc oxide (TYPE V, manufactured by Wako Pure Chemical Industries, Ltd.). The mixture was shaken while stirring at room temperature for 14 hours to obtain a clouded solution. This solution was poured into 800 ml of a 0.1% by weight aqueous polyvinyl alcohol solution maintained at 15° C. in advance. The mixture was emulsified at 8,500 rpm with a turbine-type homomixer to prepare an O/W emulsion. This O/W emulsion was stirred at room temperature for 3 hours to volatilize dichloromethane and ethanol. After solidification of an oily phase, it was collected by centrifugation at 2,000 rpm. This was dispersed into distilled water again, and the dispersion was further centrifuged to wash away freed drugs. The collected microcapsules were dispersed again by addition of a small amount of distilled water in which mannitol was dissolved, and then, the dispersion was lyophilized to obtain a powder. An encapsulation rate of Compound B in the microcapsules was 98%, and a content of Compound B in the microcapsules was 33.0%.

Reference Example 18

According to the same manner as that of Reference Example 17, microcapsules were obtained except that 0.4 ml of distilled water was added, and the shaking and stirring for 14 hours was changed to dispersing (emulsifying) and mixing of the solids (Compound B and zinc oxide) at the same rotation number for 1 minute with a homogenizer. An encapsulation rate of Compound B in the microcapsules was 97%, and a content of Compound B in the microcapsules was 32.6%.

Reference Example 19

According to the same manner as that of Reference Example 17, microcapsules were obtained except that the amount of distilled water added was changed to 0.18 ml. An encapsulation rate of Compound B in the microcapsules was 97%, and a content of Compound B in the microcapsules was 32.5%.

Reference Example 20

To a solution obtained by dissolving 7.2 g of a lactic acid-glycolic acid copolymer (lactic acid/glycolic acid 75/25 (mol %), weight average molecular weight 10,600) in 22 ml of dichloromethane and 0.8 ml of ethanol, and 0.16 ml of distilled water were added 4 g of Compound B and 0.72 g of zinc oxide (TYPE V, manufactured by Wako Pure Chemical Industries, Ltd.). To the mixture was added 0.16 ml of distilled water. Immediately after the addition, the mixture was dispersed (emulsified) and mixed with a homogenizer according to the same manner as that of Reference Example 18 to obtain a clouded solution. This was cast on a plate in the shape of a circle having a radium of about 5 cm, and dried under reduced pressure at room temperature for 15 hours to obtain a dried material. This dried material was roughly ground on a sieve having pores of 250 μm diameter, 5 g of the dried material passed through the sieve was mixed with 0.4 g of mannitol, and then, the mixture was air-ground at air pressure of 2 kg/cm$^2$ with a jet mill apparatus (A-OJET, manufactured by Seishinkigyo) to obtain fine particles having an average particle diameter of 21 μm. A content of Compound B in the fine particles was 31.0%.

Reference Example 21

A clouded solution obtained by dispersing (emulsifying) and mixing according to the same formulation and procedures as those of Reference Example 20 was spray-dried (Modile Minor, manufactured by Niro Japan) under the following conditions to obtain fine particles having an average particle diameter of 32 μm as a dried product under cyclone.

Spraying manner: twin-fluid nozzle (nozzle diameter 1.2 mm)
Air pressure: 1 kg/cm$^2$
Drying chamber inlet temperature: 90° C.
Drying chamber outlet temperature: 40-43° C.

A content of Compound B in the resulting fine particles was 28.1%.

Reference Example 22

| Capsule | |
|---|---|
| (1) Candesartan cilexetil | 30 mg |
| (2) Lactose | 90 mg |
| (3) Microcrystalline cellulose | 70 mg |
| (4) Magnesium stearate | 10 mg |
| One capsule | 200 mg |

After mixing (1), (2) and (3), and ½ of (4), they are granulated. To this is added the remaining (4), and the entire mixture is encapsulated into a gelatin capsule.

Reference Example 23

| TABLET | |
|---|---|
| (1) Candesartan cilexetil | 30 mg |
| (2) Lactose | 35 mg |
| (3) Corn starch | 150 mg |
| (4) Microcrystalline cellulose | 30 mg |
| (5) Magnesium stearate | 5 mg |
| One tablet | 250 mg |

After mixing (1), (2), (3), ⅔ of (4) and ½ of (5), they are granulated. To the granules are added the remaining (4) and (5), and the mixture is compressed into tablets.

Example 1

Prostate cancer cells, DU-145 (androgen receptor negative cell line derived from metastasis of prostate cancer) were seeded on a 6-well dish (1×10$^5$ cells/well), and cultured for 24 hours under serum free conditions. Then, EGF and 2-ethoxy-1-[[2'-(1H-tetrazol-5-yl)biphenyl-4-yl]methyl]benzimidazole-7-carboxylic acid (Compound B) were added, and 5 days after, the number of cells was counted with a hematocytometer [FIG. 1].

For each series, 3 dishes were used, and cells were grown by stimulation with EGF, but inhibition of growth was observed by addition of Compound B. In particular, by stimulation with 10$^{-6}$ M of Compound B, about 12% reduction was observed as compared with stimulation with EGF alone.

Example 2

Figure 2:
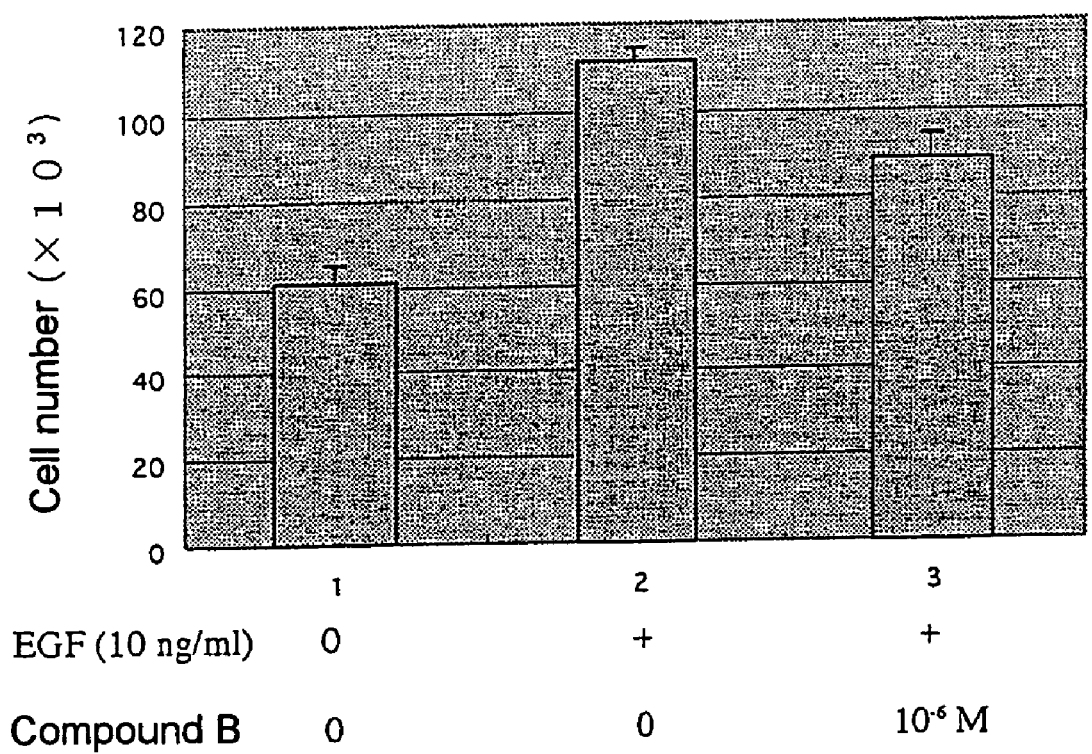
FIG. 2 shows the results of measurement of the cell number of LNCaP cells in 5 days after addition of EGF and Compound B.

Prostate cancer cells, LNCaP (androgen receptor positive cell line derived from metastasis of prostate cancer) were seeded on a dish (1×10$^5$ cells/dish), and cultured for 24 hours under serum free conditions. Then, EGF and Compound B were added, and 5 days after, the number of cells was counted [FIG. 2].

For each series, 3 dishes were used, and cells were grown by stimulation with EGF, but inhibition of growth was observed by addition of Compound B. In addition, by stimulation with 10$^{-6}$ M of Compound B, about 22% reduction was observed as compared with stimulation with EGF alone.

Both LNCaP and DU145 prostate cancer cells have an angiotensin II receptor (AT1) (This has been already confirmed by mRNA level). In both cells, increase in the number of cells is observed by stimulation with EGF which is a growth factor, but the growth is inhibited by Compound B which is a blocker of an angiotensin II receptor AT1. This can be considered as follows: Compound B has inhibitory action on intracellular signal transduction of EGF and, consequently, cell growth is inhibited. Since LNCaP cells are androgen-dependent cells, and DU145 cells are androgen-independent cells, it is presumed that Compound B has the effect of inhibiting growth of prostate cancer cells irrespective of androgen dependency.

Example 3

Figure 3:
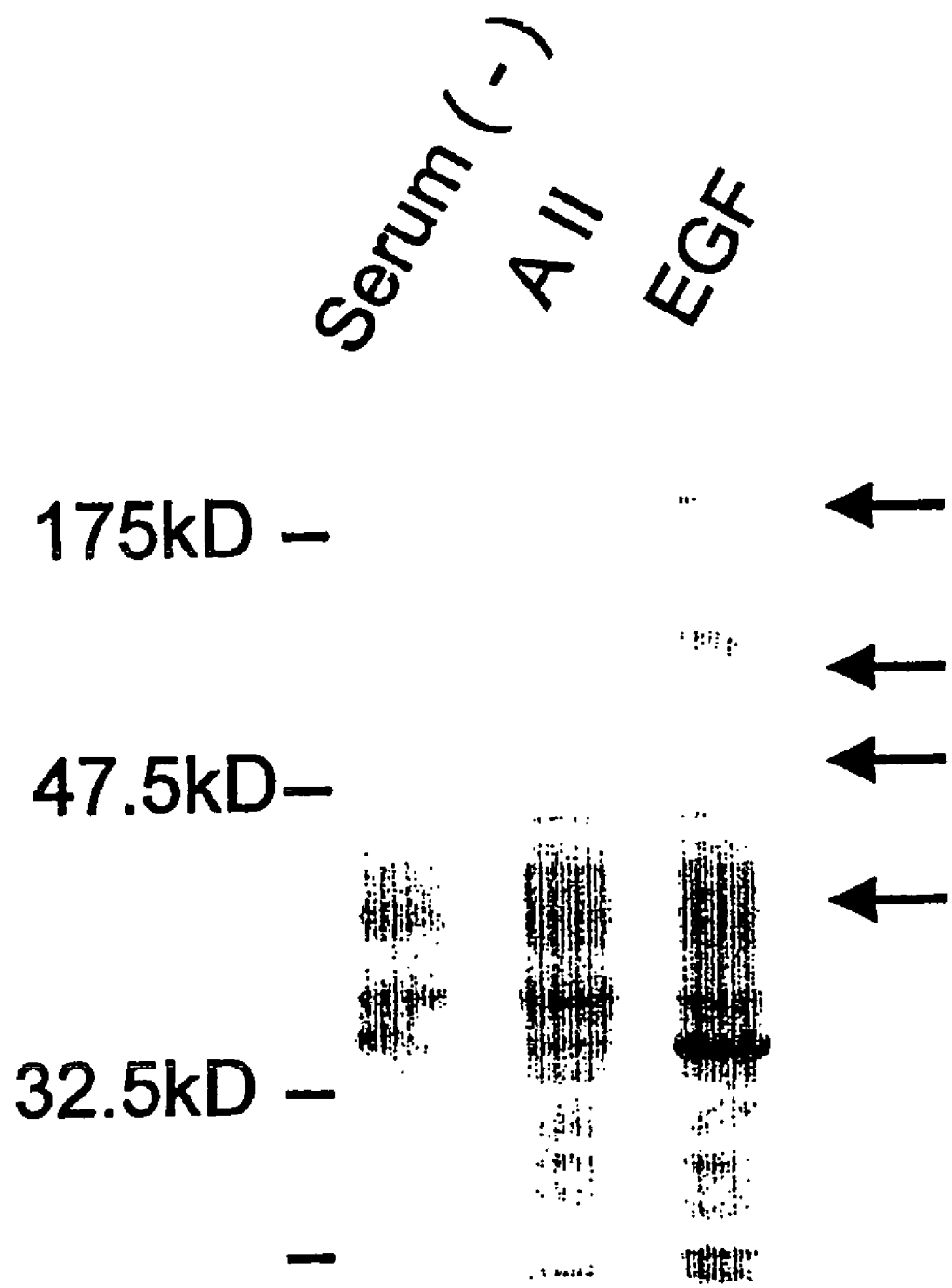
FIG. 3 shows the results of observation of tyrosine phosphorylation of an intracellular protein due to stimulation of LNCaP cells with angiotensin II and EGF.

It is already known that, when growth stimulation such as EGF is applied to cells, phosphorylation of cellular proteins is induced by activation of signal transduction pathway. Then, in order to make clear the effect of angiotensin II on prostate cancer, prostate cancer LNCaP cells were cultured for 24 hours with no serum stimulation, and then, the culture was stimulated with angiotensin II ($1 \times 10^{-6}$ M) or EGF (1 ng/ml) which was already known to have growth promoting effect, and 5 minutes after, cells were collected. The whole cell lysate separated by SDS-PAGE, transferred onto a PVDF membrane, and then tyrosine phosphorylation of an cellular protein was observed by Western blotting method using an anti-phospho-tyrosine antibody (Upstate, 10 Old Barn Road Lake Placid, N.Y. 12946 U.S.A.) [FIG. 3]. For several cellular proteins, tyrosine phosphorylation was induced by stimulation with EGF as compared with the state before application of stimulation. At the same time, like the stimulation with EGF, tyrosine phosphorylation of the same protein by stimulation with angiotensin II was also observed as shown by the arrows. That is, it is considered that stimulation with angiotensin II has the same or similar effect as that of stimulation with EGF on prostate cancer cells. From this, it is considered that Compound B which inhibits stimulation with angiotensin II consequently inhibits growth of prostate cancer cells.

Example 4

Figure 4:
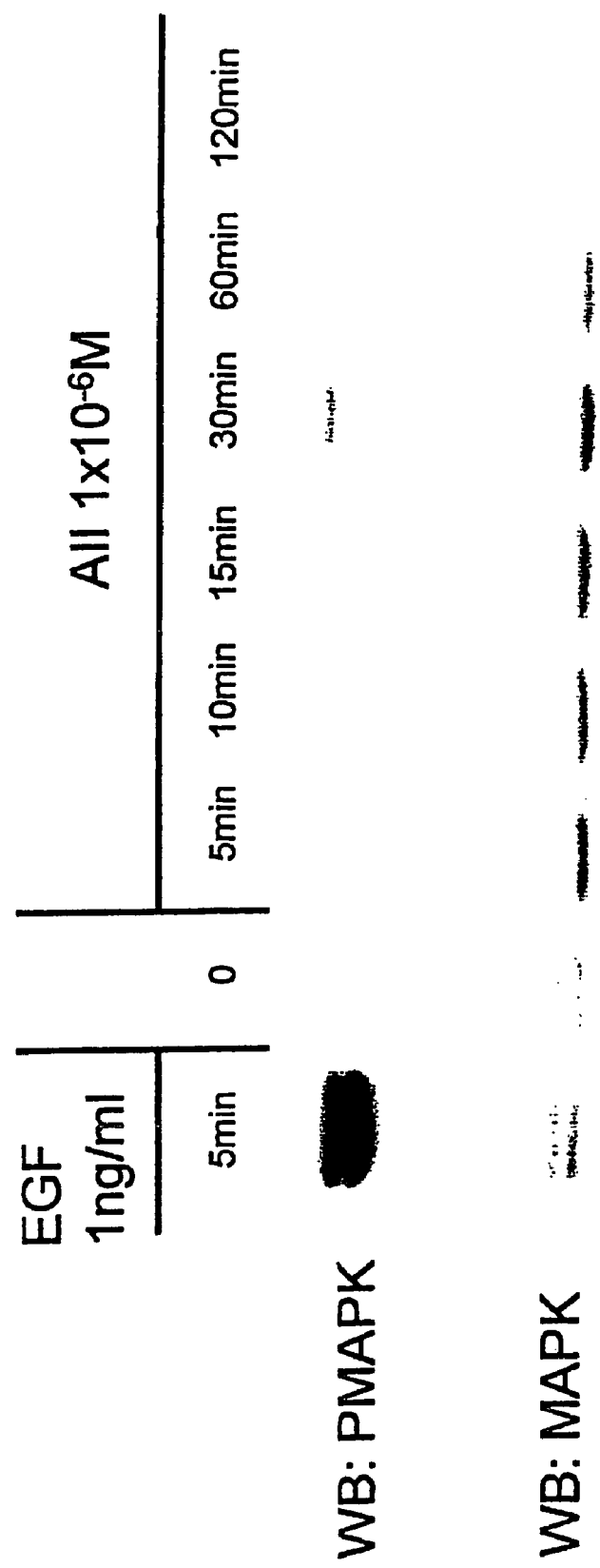
FIG. 4 shows the results of measurement of intracellular activated MAP kinase due to stimulation of LNCaP cells with angiotensin II and EGF and the total amount of MAP kinase.

In order to make clear the effect of angiotensin II on MAP kinase which is one of cellular proteins controlling cell growth, prostate cancer LNCaP cells were cultured for 24 hours with no serum stimulation, and then, stimulated with angiotensin II ($1 \times 10^{-6}$ M) or EGF (1 ng/ml) already known to have growth promoting effect, and cells were collected at an appropriate time. The whole cell lysate was separated by SDS-PAGE, and then, transferred onto a PVDF membrane, and a total amount of cellular activated MAP kinase and MAP kinase was measured by Western blotting method using an anti-phospho-MAP kinase antibody which recognizes only activated MAP kinase (Cell Signaling Technology, 166B Cumming Center Beverly, Mass. 01915 U.S.A.: in FIG. 4, WB: PMAPK), and a MAP kinase antibody which recognizes all endogenous MAP kinases (Cell Signaling Technology, 166B Cumming Center Beverly, Mass. 01915 U.S.A.: in FIG. 4, WB: MAPK) [FIG. 4]. When stimulation with angiotensin II or EGF was applied, activated MAP kinase was increased (in FIG. 4, WB: PMAPK), though no change in a total amount of MAP kinases was observed (in FIG. 4, WB: MAPK). That is, it has been apparent that MAP kinase controlling cell growth is activated by stimulation of angiotensin II. From this, it is considered that Compound B which inhibits stimulation with angiotensin II consequently inhibits growth of prostate cancer cells.

Example 5

Figure 5:
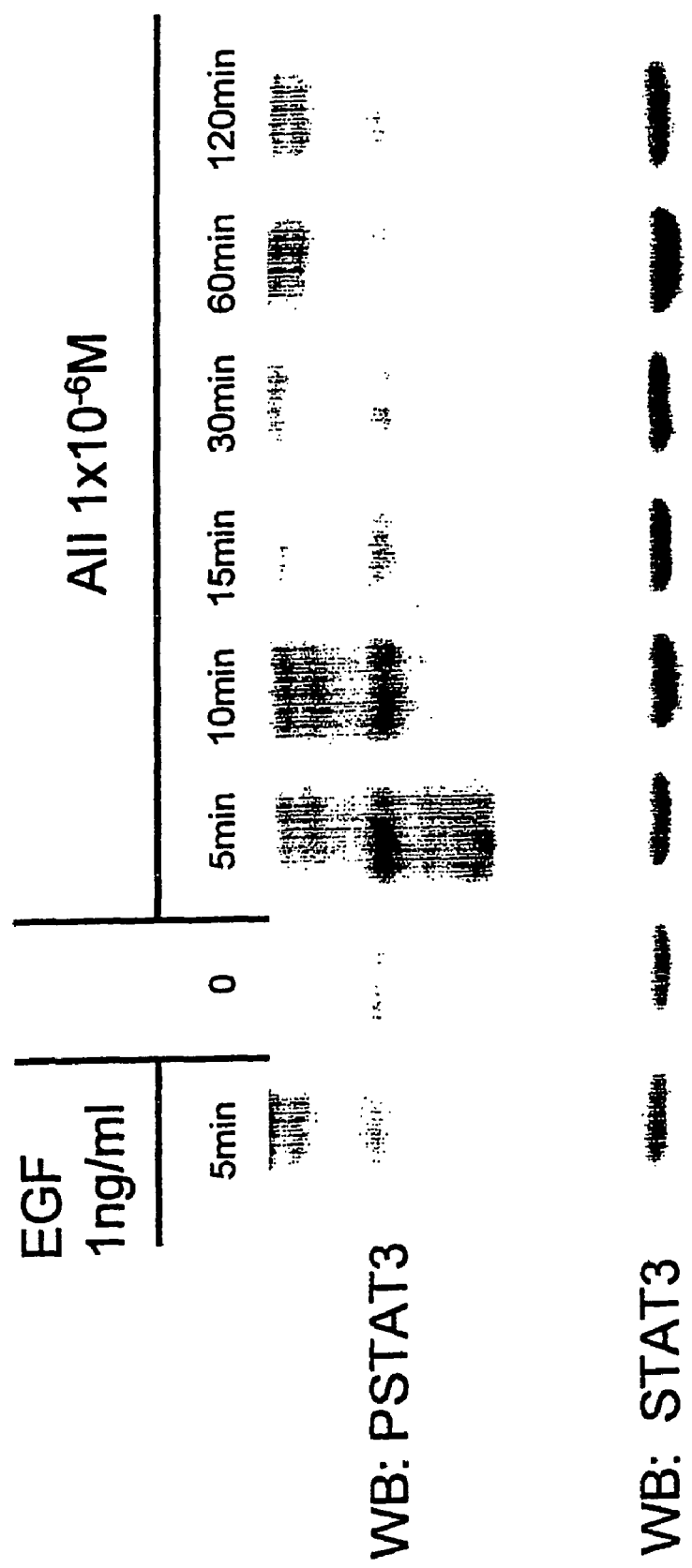
FIG. 5 shows the results of measurement of intracellular activated STAT3 due to stimulation of LNCaP cells with angiotensin II and EGF and the total amount of STAT3.

In order to make clear the effect of angiotensin II on an cellular protein STAT3 which is one of signal transducing molecules of a growth factor and a cytokine and is said to be involved in cell growth, prostate cancer LNCaP cells were cultured for 24 hours with no serum stimulation, and then, stimulated with angiotensin II ($1 \times 10^{-6}$ M) or EGF (1 ng/ml) already known to have growth promoting effect, and cells were collected at an appropriate time. The whole cell lysate was separated by SDS-PAGE, and then, transferred onto a PVDF membrane. Activated STAT3 and a total amount of STAT3 were confirmed by Western blotting method using an anti-phospho-STAT3 (Tyr705) antibody which recognizes only activated STAT3 (Cell Signaling Technology, 166B Cumming Center Beverly, Mass. 01915 U.S.A.: in FIG. 5, WB: PSTAT3), and a STAT3 antibody which recognizes all endogenous STAT3s (Cell Signaling Technology, 166B Cumming Center Beverly, Mass. 01915 U.S.A.: in FIG. 5, WB: STAT3) [FIG. 5]. When stimulation with angiotensin II or EGF was applied, activated STAT3 was increased (in FIG. 5, WB: PSTAT3), though no change in a total amount of STAT3 was observed (in FIG. 5, WB: STAT3). That is, it has been apparent that STAT3 controlling cell growth is activated by stimulation with angiotensin II. From this, it is considered that Compound B which inhibits stimulation with angiotensin II consequently inhibits growth of prostate cancer cells.

Example 6

Figure 6:
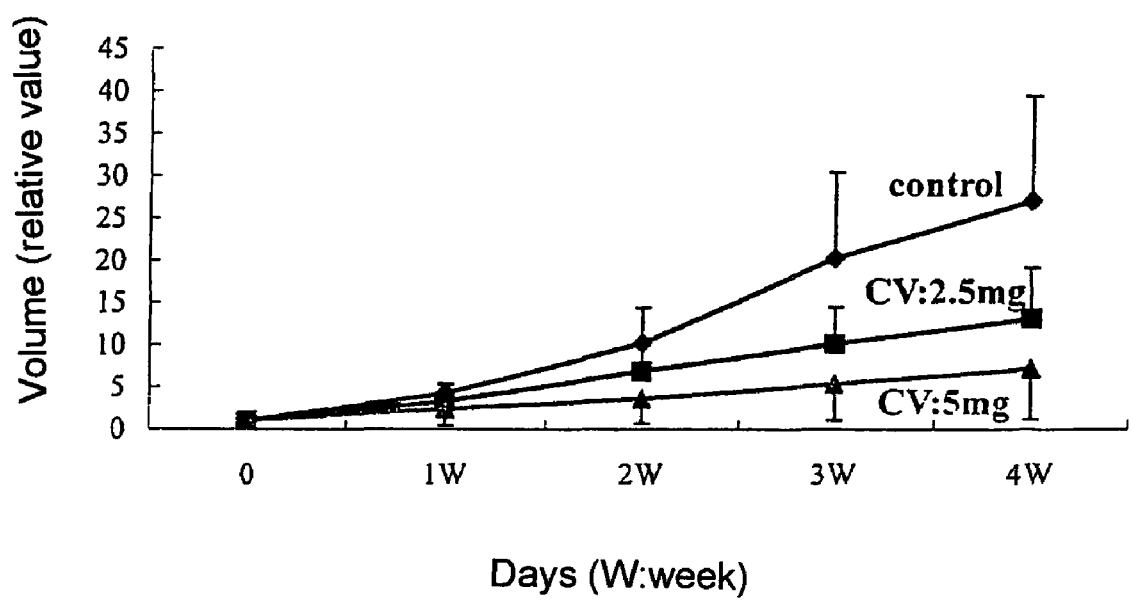
FIG. 6 shows the change in tumor proliferation with time in case where a tumor is formed in a 4 week old male nude mouse (Balb/c) with DU145 cells. -♦- indicates a control (control group), -■- indicates a Compound C 5 mg/kg/day-administered group, and -▲- indicates a Compound C 2.5 mg/kg/day-administered group.

To a male 4 week-old nude mouse (Balb/c), $5 \times 10^6$ DU145 cells were subcutaneously injected on a back. After 10 days, when tumor having a diameter of 5 mm was formed (week 0), Candesartan cilexetil (Compound C) was mixed into drinking water so that Compound C could be orally taken at a dosage of 5 mg/kg day or 2.5 mg/kg day (each group: n=5). As a control group, a group (n=5) receiving no Compound C was bred at the same time. Initiation of the oral administration was regarded as week 0, each group was bred for 4 weeks, and a diameter of tumor was measured every week. The results are shown in FIG. 6. From week 2, inhibition of tumor growth was observed in a Compound C-administered group. In particular, it was recognized that a Compound C: 5 mg/kg/day administered group had a difference in growth inhibition as compared with the control group, with a significant difference of P<0.01, in and after week 2.

Example 7

Figure 7:
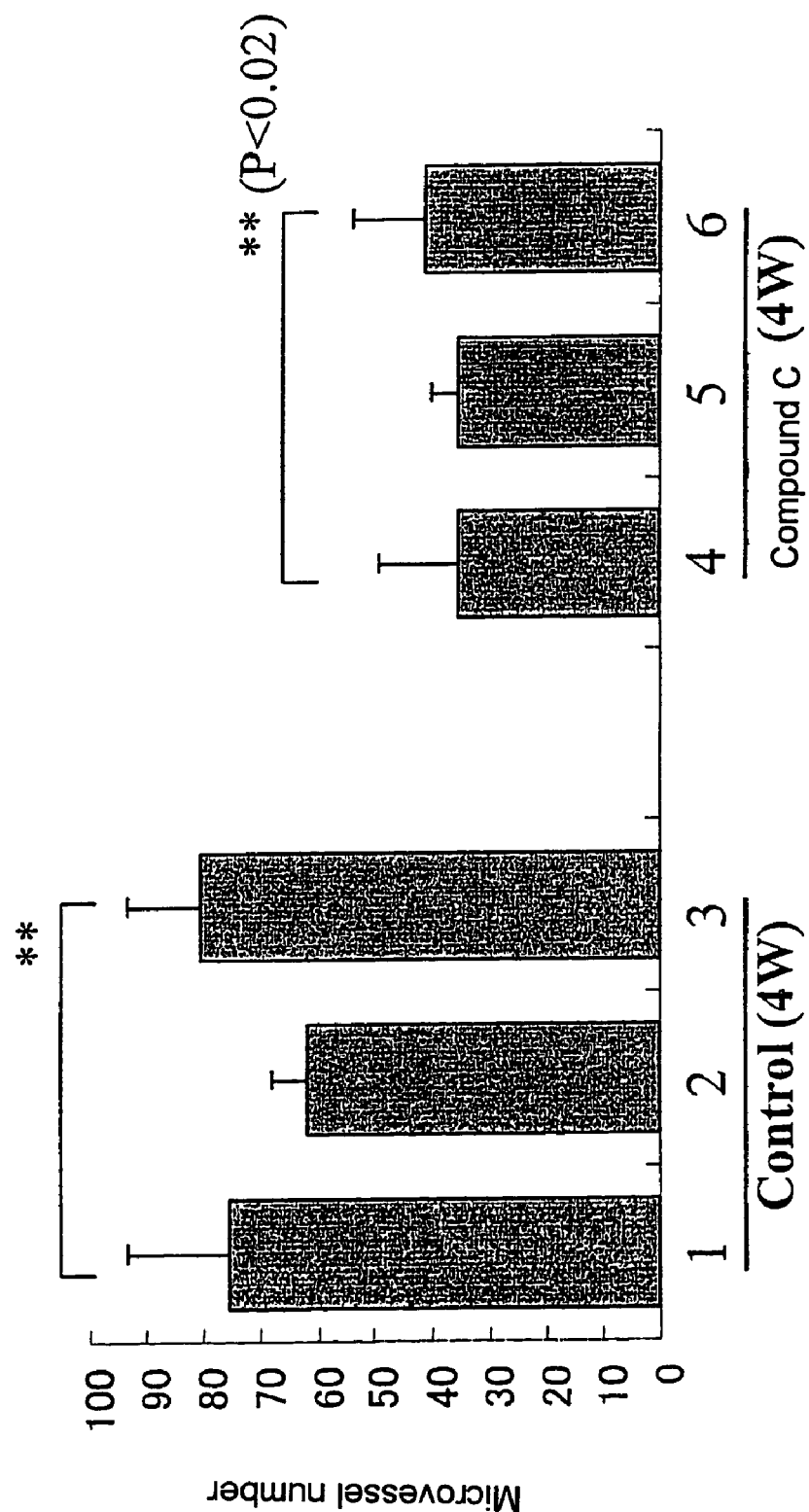
FIG. 7 shows the results of measurement of the number of microvessels in tumor in a control group (control) and a Compound C 5 mg/kg/day-administered group in case where a tumor is formed in a 4 week old male nude mouse (Balb/c) with DU145 cells.

To a male 4 week old nude mouse (Balb/c), $5 \times 10^6$ DU145 cells were subcutaneously injected on a back. After 10 days, when tumor having a diameter of 5 mm was formed (0 week), Candesartan cilexetil (Compound C) was mixed into drinking water (each group: n=3) so that Compound C could be orally taken the an amount of 5 mg/kg/day. As a control group, a group (n=3) receiving no Compound C was bred at the same time. Initiation of the oral administration was regarded as week 0, each group was bred for 4 weeks, and thereafter, tumor was isolated, stained with an anti-CD31 antibody as described hereinafter, and the number of microvessels in tumor was examined. Under a microscope (magnification 400), four places rich in the number of microvessels were selected from a tumor solid tissue part, and the number was counted. The results are shown in [FIG. 7]. Average 72.5±9.7 vessels were recognized in one field in case of the control group, and average 37.5±3.3 vessels were recognized in one field in case of the Compound C-administered group and, thus, a significant difference was recognized between both groups (P<0.02). It was confirmed that vascularization was significantly decreased in the Compound C-administered group (B) as compared with the control group (A).

CD31 Immunological Tissue Chemical Staining:

Vessels in a tumor-transplanted tissue of a nude mouse were immunologically stained using an anti-mouse CD31 antibody, and the number of vessels and vascularization state were studied. Procedures were as follows:

To a male 4 week old nude mouse (Balb/c), $5 \times 10^6$ DU145 cells were subcutaneously injected on a back, and 10 days after, tumor having a diameter of 5 mm was formed. Then, the mouse orally ingested Candesartan cilexetile at a dosage of 5 mg/kg/day, and tumor was isolated after 4 weeks. Isolated tumor was divided into two and placed on a cryomold with a side to be cut into pieces down, and thereafter, OCT compound was poured therein, followed by freezing. The frozen tissue was cut into pieces having a thickness of 2.5 μm, and air-dried. Then, pieces were acetone-fixed for 5 minutes on an ice. After immersion in water at room temperature for 5 minutes, pieces were placed in 0.3% hydrogen peroxide/methanol at room temperature for 30 minutes in order to inactivate endogenous peroxidase. The specimen was immersed in water and PBS for 5 minutes, respectively, and placed in 10% normal goat serum/PBS at 37° C. for 15 minutes. Then, the specimen was exposed to an anti-mouse CD31 (PECAM) monoclonal antibody (25 to 100-fold dilution) (Pharmingen, Cat01951D) at 37° C. for 1 hour and at 4° C. for 8 hours. The specimen was immersed in PBS three times for each 5 minutes, and thereafter, reacted with biotinated anti-rat IgG (100-fold dilution) (Pharmingen, Cat 554014) at 37° C. for 30 minutes. The specimen was washed with PBS three times for each 5 minutes, and reacted with streptoavidin-labelled peroxidase (Nichirei, Histofine kit) at room temperature for 5 minutes. The specimen was washed with PBS three times, and transferred into water. As diaminobenthidine (DAB) reaction, the specimen was immersed into 0.3 g DAB/0.1% Tween 20/150 ml PBS with a few droplets of hydrogen peroxide added thereto, transferred to water every 15 seconds to stop the reaction, and the reaction was stopped at an appropriate time while observing with a microscope. After washed with water, the specimen was stained (hematoxylin or methyl green), and dehydration-sealed routinely.

Example 8

Figure 8:
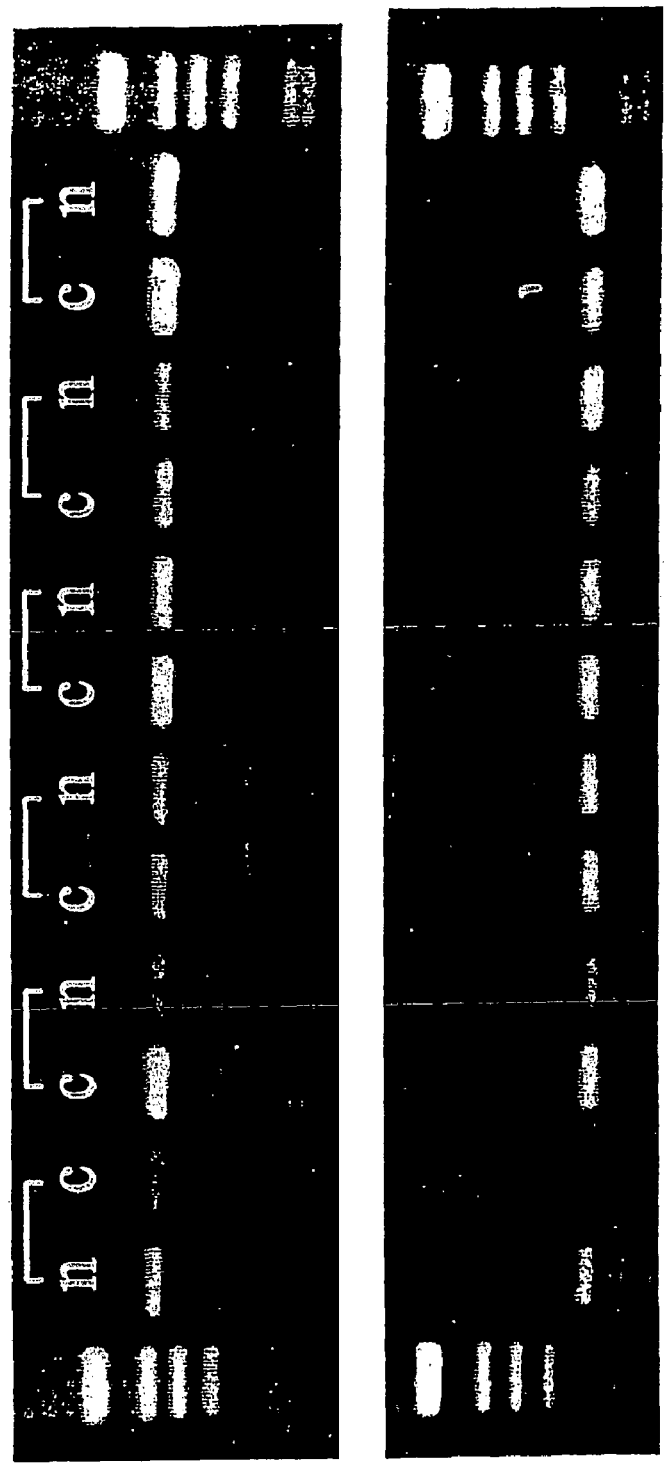
FIG. 8 shows the results of investigation of AT1 mRNA expression in prostate cancer tissue by RT-PCR.

Expression of mRNA of angiotensin II receptor (AT1) in a prostate cancer tissue was examined by RT-PCR. A total RNA was extracted from a prostate cancer tissue obtained by radical prostatectomy, and from a normal prostate tissue of the same specimen, and converted into a cDNA, followed by PCR. At the same time, as an internal control, β-actin was also subjected to PCR, and 10 μl of each PCR product was subjected to electrophoresis using a 1.5% agarose gel. As shown in [FIG. 8], bands of AT1 and β-actin were quantitated by NIH Image, and an amount of AT1 expression was semi-quantitated by measuring an AT1/β-actin ratio. PCR primers are as follows:

```
AT1:
                              [SEQ ID NO: 1]
5'-GTAGCCAAAGTCACCTGCATC-3',

[SEQ ID NO: 2]
5'-CAGTCACGTATGATGCCTAGT-3'

β-actin:
                              [SEQ ID NO: 3]
5'-TAATACGACTCACTATAGGGAGA
GCGGGAAATCGTGCGTACATT-3',

[SEQ ID NO: 4]
5'-GATGGAGTTGAAGGTAGTTTCGTG-3'.
```

Figure 9:
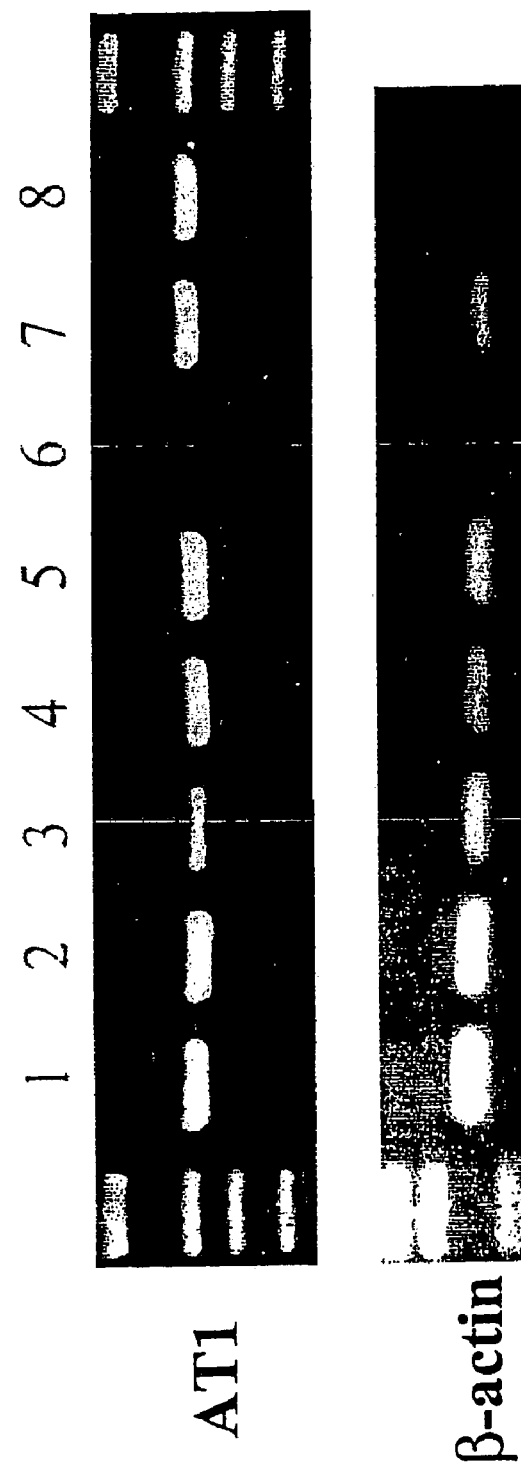
FIG. 9 shows the results of investigation of AT1 mRNA expression in recrudescent prostate cancer tissue by RT-PCR.

The PCR conditions are as follows:
denaturing 30 seconds, 95° C., annealing 30 seconds, 55° C., elongation 30 seconds, 72° C., AT1: total 30 cycles, beta-actin: total 23 cycles As a result, the number of cases, where mRNA of AT1 was strongly expressed in a cancer tissue as compared with a normal tissue, was 15 (62.5%) among 24, and it was presumed that AT1 is expressed stronger in a cancer tissue. In addition, expression of mRNA of AT1 in a relapsed prostate cancer tissue was examined by RT-PCR. Regarding the tissue, a total RNA was extracted from a recrudescent prostate primary lesion, metastasized lymph node, and a bone tissue, and converted into a cDNA, followed by PCR. At the same time, as an internal control, β-actin was also subjected to PCR, and 10 μl of each PCR product was subjected to electrophoresis using a 1.5% agarose gel. The results are shown in [FIG. 9]. It was recognized that expression of AT1 mRNA in a relapsed cancer tissue is strong.

Example 9

As cases, there were 11 cases of relapsed prostate cancer, and an average age at recrudescence was 70.8 old (list of cases is shown in [FIG. 10]). As initial therapy, one case was receiving radical prostatectomy (case 2), other cases were receiving hormone therapy. Among them, 4 cases were receiving radiation therapy by external irradiation as supplemental therapy. 10 Cases have bone metastasis and lymph node/lung metastasis and, in all 11 cases, a serum PSA value was increased successively three times and no reduction in a PSE value due to androgen withdrawal was recognized. As an administration method of Candesartan, 4 mg tablets were administered starting from one tablet per day in cases where a systolic pressure at hospital visit was 140 mmHg or higher.

Bropress tablets were administered to 11 cases of relapsed prostate cancer patients, and the results are shown below. Administration was limited to cases where ingestion was possible for consecutive 15 weeks or longer. Assessment of a serum SPA value was performed by dividing a maximum value by a minimum reduction value in bropress ingestion, reduction of 50% or larger was recognized in 3 (27.3%) among 11 cases, and reduction of 50% or smaller was recognized in 2 cases (18.2%). Therefore, reduction in a PSA value was recognized in a total of 5 cases (45.5%). An ingestion period from initiation of bropress ingestion to recognition of reduction in a PSA value was average 14.7 weeks in reduction of PSA 50% or larger, and average 20 weeks in reduction of PSA 50% or smaller. The ingestion period was average 16.8 weeks in all cases of reduction in a PSA value.

Example 10

Figure 11:
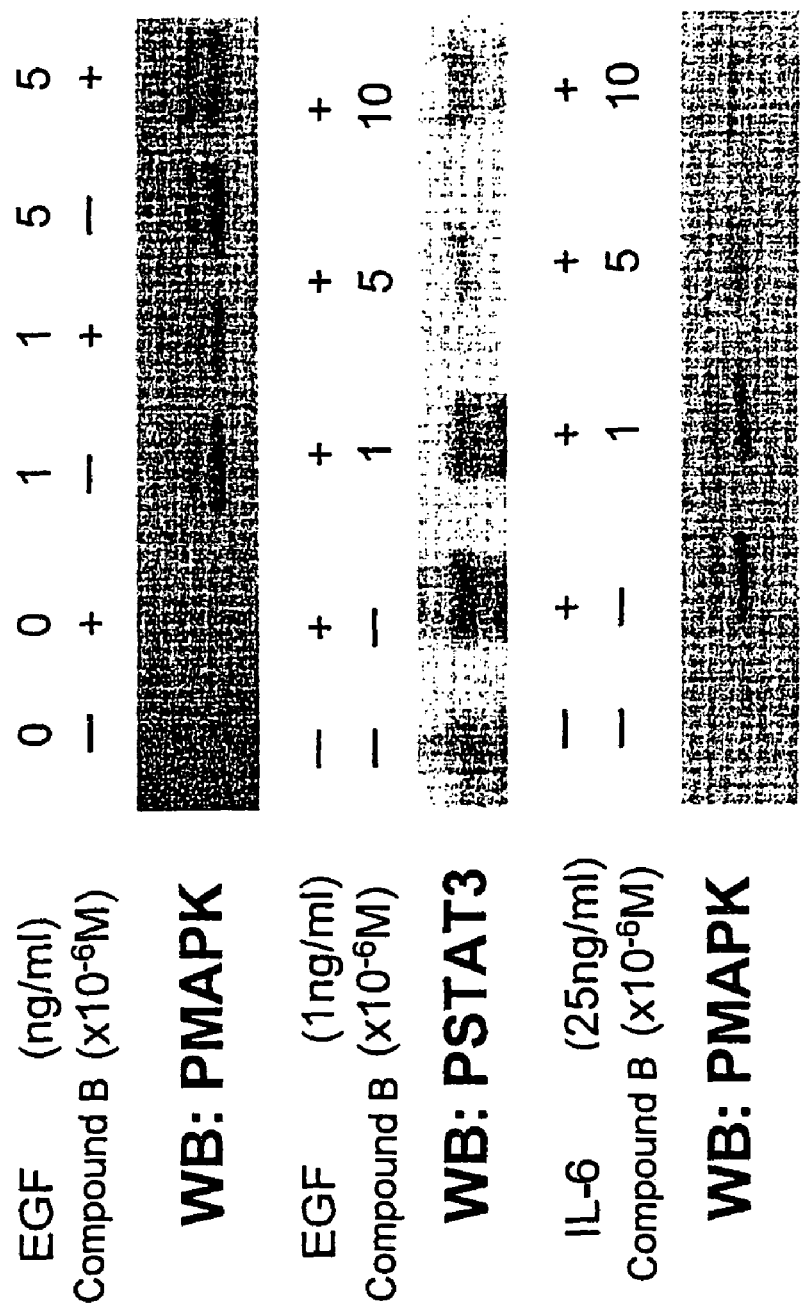
In FIG. 11, the upper column shows the results obtained by culturing LNCaP cells ($10^7$ cells) in a serum-free culturing solution for 24 hours, adding each concentration of EGF and Compound B ($10^{-6}$ M), and investigating phosphorylation of MAPK. The middle column shows the results obtained by culturing LNCaP cells ($10^7$ cells) in a serum-free culturing solution for 24 hours, adding EGF: 1 ng/ml and each concentration of Compound B ($10^{-6}$ M, $5\times10^{-6}$ M, $10\times10^{-6}$ M), and investigating phosphorylation of MAPK. The lower column shows results obtained by culturing LNCaP cells ($10^7$ cells) in a serum-free culturing solution for 24 hours, adding IL-6 25 ng/ml and each concentration of Compound B ($10^{-6}$M, $5\times10^{-6}$M, $10\times10^{-6}$M), and investigating phosphorylation of MAPK.

(1) LNCaP cells ($10^7$ cells) were cultured in a serum-free culture medium (F-12+1 mg/ml BSA) for 24 hours, each concentration of EGF and Compound B ($10^{-6}$ M) were added, and phosphorylation of MAPK was investigated. The results are as follows: When stimulated with EGF: 1 ng/ml, MAPK was phosphorylated, while phosphorylation was inhibited by addition of Compound B ($10^{-6}$ M) before 30 minutes [FIG. 11, upper column].

(2) LNCaP cells ($10^7$ cells) were cultured in a serum-free culture medium (F-12+1 mg/ml BSA) for 24 hours, EGF: 1 ng/ml and each concentration of Compound B ($10^{-6}$ M, $5\times10^{-6}$ M, $10\times10^{-6}$ M) were added, and phosphorylation of MAPK was investigated. The results are as follows: it was recognized that phosphorylation of STAT3 by EGF stimulation was inhibited in a Compound B dose dependant manner [FIG. 11, middle column].

(3) LNCaP cells ($10^7$ cells) were cultured in a serum-free culture medium (F-12+1 mg/ml BSA) for 24 hours, IL-6: 25 ng/ml and each concentration of Compound B ($10^{-6}$ M, $5\times10^{-6}$ M, $10\times10^{-6}$ M) were added, and phosphorylation of MAPK was investigated. The results are as follows: it was recognized that phophorylation of MAPK by IL-6 was inhibited in a Compound B dose dependent manner [FIG. 11, lower column].

From the foregoing, it has been presumed that Compound B inhibits MAPK of EGF and IL-6, and phosphorylation of STAT3 and, consequently, causes inhibition of cell growth.

INDUSTRIAL APPLICABILITY

A compound having an angiotensin II antagonism, its pro-drug or a pharmaceutically acceptable salt thereof can inhibit (block) intracellular signaling by MAP kinase STAT3 which plays a central role in signal transduction of cell proliferation, and can inhibit tyrosine phosphoryration of cellular proteins.

Therefore, the anticancer agents of the present invention such as the remedy or the preventive for hormone-independent cancer, the hormone-independent cancer cell proliferation inhibitor, and the cancer cell apoptosis inducer exert excellent anticancer action, and have no side effects and, therefore, have excellent nature as a medicament. In addition, since the anticancer agents of the present invention show significant effects on cancer for which a conventional vascularization inhibitor cannot provide effective therapeutic effects, they are also effective in that they can also be used for cancer not necessarily requiring vascularization.

The invention claimed is:

1. A method for treating hormone-independent prostate cancer, which comprises administering a combination of a non-peptidic compound having an angiotensin II antagonism selected from the group consisting of 2-ethoxy-1-[[2'-(1H-tetrazol-5-yl)biphenyl-4-yl]methyl]benzimidazole-7-carboxylic acid and 1-(cyclohexyloxycarbonyloxy)ethyl 2-ethoxy-1-[[2'-(1H-tetrazol-5-yl)biphenyl-4-yl]methyl]benzimidazole-7-carboxylate, or a salt thereof, and a LH-RH agonist or antagonist selected from the group consisting of leuprorelin, goserelin, buserelin, triptorelin, nafarelin, histrelin, deslorelin, meterelin, gonadrelin and a peptide represented by the formula:

X-D2Nal-D4ClPhe-D3Pal-Ser-A-B-Leu-C-Pro-DAla-NH$_2$ wherein X denotes N(4H$_2$-furoyl)Gly or NAc, A denotes a residue selected from NMeTyr, Tyr, Aph(Atz) and NMeAph (Atz), B denotes a residue selected from Dlys(Nic), DCit, Dlys(AzaglyNic), DLys(AzaglyFur), DhArg(Et$_2$), DAph (Atz) and DhCi, C denotes Lys(Nisp), Arg or hArg(Et$_2$), or a salt thereof to a mammal having hormone-independent prostate cancer in an amount effective to treat hormone-independent prostate cancer.

2. The method according to claim 1, wherein the non-peptidic compound having an angiotensin II antagonism is 2-ethoxy-1-[[2'-(1H-tetrazol-5-yl)biphenyl-4-yl]methyl]benzimidazole-7-carboxylic acid.

3. The method according to claim 1, wherein the non-peptidic compound having an angiotensin II antagonism is 1-(cyclohexyloxycarbonyloxy)ethyl 2-ethoxy-1-[[2'-(1H-tetrazol-5-yl)biphenyl-4-yl]methyl]benzimidazole-7-carboxylate.

4. The method for treating hormone-independent prostate cancer of claim 1, wherein the hormone-independent prostate cancer is hormone-independent prostate cancer in which a clinically clear metastasized lesion is observed.

5. The method for treating hormone-independent prostate cancer of claim 1, which consists of administering a combination of a non-peptidic compound having an angiotensin II antagonism selected from the group consisting of 2-ethoxy-1-[[2'-(1H-tetrazol-5-yl)biphenyl-4-yl]methyl]benzimidazole-7-carboxylic acid and 1-(cyclohexyloxycarbonyloxy)ethyl 2-ethoxy-1-[[2'-(1H-tetrazol-5-yl)biphenyl-4-yl]methyl]benzimidazole-7-carboxylate, or a salt thereof and a LH-RH agonist or antagonist selected from the group consisting of leuprorelin, goserelin, buserelin, triptorelin, nafarelin, histrelin, deslorelin, meterelin, gonadrelin and a peptide represented by the formula:

X-D2Nal-D4ClPhe-D3Pal-Ser-A-B-Leu-C-Pro-DAla-NH$_2$ wherein X denotes N(4H$_2$-furoyl)Gly or NAc, A denotes a residue selected from NMeTyr, Tyr, Aph(Atz) and NMeAph (Atz), B denotes a residue selected from Dlys(Nic), DCit, Dlys(AzaglyNic), DLys(AzaglyFur), DhArg(Et$_2$), DAph (Atz) and DhCi, C denotes Lys(Nisp), Arg or hArg(Et$_2$), or a salt thereof to a mammal having hormone-independent prostate cancer in an amount effective to treat hormone-independent prostate cancer.

6. A method for treating hormone-independent prostate cancer, which comprises administering a non-peptidic compound having an angiotensin II antagonism selected from the group consisting of 2-ethoxy-1-[[2'-(1H-tetrazol-5-yl)biphenyl-4-yl]methyl]benzimidazole-7-carboxylic acid and 1-(cyclohexyloxycarbonyloxy)ethyl 2-ethoxy-1-[[2'-(1H-tetrazol-5-yl)biphenyl-4-yl]methyl]benzimidazole-7-carboxylate, or a salt thereof to a mammal having hormone-independent prostate cancer in an amount effective to treat hormone-independent prostate cancer.

7. The method according to claim 6, wherein the non-peptidic compound having an angiotensin II antagonism is 1-(cyclohexyloxycarbonyloxy)ethyl 2-ethoxy-1-[[2'-(1H-tetrazol-5-yl)biphenyl-4-yl]methyl]benzimidazole-7-carboxylate.

8. The method according to claim 6, wherein the hormone-independent prostate cancer is hormone-independent prostate cancer in which a clinically clear metastasized lesion is observed.

9. The method according to claim 4 or 8, wherein the mammal is a patient having stage D prostate cancer.

10. The method according to claim 4 or 8, wherein the mammal is a patient having stage D2 prostate cancer.

* * * * *